(12) United States Patent
Kitagawa

(10) Patent No.: US 12,024,720 B2
(45) Date of Patent: Jul. 2, 2024

(54) CELL CULTIVATION METHOD, CELL SUPPORT COMPOSITE PRODUCTION METHOD, CULTIVATED CELLS, AND CELL SUPPORT COMPOSITE

(71) Applicant: NIKKISO CO., LTD., Tokyo (JP)

(72) Inventor: Fumihiko Kitagawa, Kanazawa (JP)

(73) Assignee: NIKKISO CO., LTD., Tokyo (JP)

( * ) Notice: Subject to any disclaimer, the term of this patent is extended or adjusted under 35 U.S.C. 154(b) by 196 days.

(21) Appl. No.: 16/593,462

(22) Filed: Oct. 4, 2019

(65) Prior Publication Data

US 2020/0032216 A1 Jan. 30, 2020

Related U.S. Application Data

(63) Continuation of application No. PCT/JP2018/011392, filed on Mar. 22, 2018.

(30) Foreign Application Priority Data

Apr. 6, 2017 (JP) .................................. 2017-075828

(51) Int. Cl.
C12N 5/071 (2010.01)

(52) U.S. Cl.
CPC ........ *C12N 5/0686* (2013.01); *C12N 2500/30* (2013.01); *C12N 2533/52* (2013.01); *C12N 2533/54* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 2008/0166328 A1 | 7/2008 | Harmon et al. | |
| 2008/0267921 A1 | 10/2008 | Marban et al. | |
| 2011/0318725 A1 | 12/2011 | Suenaga et al. | |
| 2016/0281062 A1 | 9/2016 | Zink et al. | |

FOREIGN PATENT DOCUMENTS

| | | |
|---|---|---|
| EP | 3608398 A1 | 2/2020 |
| JP | 2003219865 A | 8/2003 |
| JP | 2011030453 A | 2/2011 |
| JP | 2011050358 A | 3/2011 |
| JP | 2014515270 A | 6/2014 |
| JP | 2015511487 A | 4/2015 |
| WO | WO-2008/047760 A1 | 4/2008 |
| WO | WO-2010/103748 A1 | 9/2010 |
| WO | WO-2011/141914 A1 | 11/2011 |
| WO | WO-2013/187359 A1 | 12/2013 |
| WO | WO-2015/167003 A1 | 11/2015 |
| WO | WO-2016019168 A1 | 2/2016 |
| WO | WO-2016/063935 A1 | 4/2016 |
| WO | WO-2017/082024 A1 | 5/2017 |
| WO | WO-2017/082025 A1 | 5/2017 |
| WO | WO-2017/082026 A1 | 5/2017 |
| WO | WO-2017/126647 A1 | 7/2017 |
| WO | WO-2018/186185 A1 | 10/2018 |

OTHER PUBLICATIONS

Andersen et al., J Am Soc Nephrol 9: 1153-1168, 1998 (Year: 1998).*
Wohlfarth et al., (Kidney International, vol. 63, Supplement 84 (2003), pp. S103-S109 (Year: 2003).*
Hall et al., Proc. Natl. Acad. Sci. USA, vol. 79, pp. 4672-4676, Aug. 1982, Cell Biology (Year: 1982).*
Hoppensack et al., Tissue Engineering: Part C, vol. 20, No. 7, 2014 (Year: 2014).*
Tufro et al (2017) Podocyte Shape Regulation by Semaphorin 3A and MICAL-1. In: Terman J. (eds) Semaphorin Signaling. Methods in Molecular Biology, vol. 1493. Humana Press, New York, NY, First Online Oct. 28, 2016 (Year: 2016).*
Forbes et al., Am J Physiol Renal Physiol 301: F110-F117, 2011 (Year: 2011).*
Written Opinion of IPEA with an English translation issued in corresponding PCT application No. PCT/JP2019/011389 on Mar. 31, 2020.
Office Action of corresponding JP Application No. 2019-511143 and English translation, dated Sep. 23, 2020, 8 pages.
International Preliminary Examination Report on Patentability of PCT/JP2019/011389 and English translation, dated Jun. 16, 2020, 21 pages.
Prange et al., "Human proximal tubule vells form functional microtissues," Pflugers Arch—Eur J Physiol (2016) vol. 468, pp. 739-750.
Office Action mailed Apr. 27, 2021 in JP Application No. 2019-511143, 8 pages.
Office Action mailed Jun. 29, 2021 in JP Application No. 2019-507828, 8 pages.
Kusamori et al.; Development of Multicellular Spheroid for Cell-Based Therapy; Drug Delivery System; 2013; 28-1; pp. 45-53; Department of Biopharmaceutics and Drug Metabolism; Graduate School of Pharmaceutical Sciences, Kyoto University.
Buzhor, Ph.D. et al.; Kidney Spheroids Recapitulate Tubular Organoids Leading to Enhanced Tubulogenic Potency of Human Kidney-Derived Cells; Tissue Engineering: Part A; 2011; pp. 2305-2319; vol. 17, Nos. 17 and 18; Mary Ann Liebert, Inc.
Gao et al.; Basic Structure and Cell Culture Condition of a Bioartificial Renal Tubule on Chip Towards a Cell-Based Separation Microdevice; Analytical Science; Sep. 2011; pp. 907-912; vol. 27; The Japan Society for Analytical Chemistry.

(Continued)

*Primary Examiner* — Evelyn Y Pyla
(74) *Attorney, Agent, or Firm* — Muncy, Geissler, Olds & Lowe, P.C.

(57) ABSTRACT

A cell cultivation method includes cultivating dedifferentiated kidney cells in a state of being non-adherent to a culture vessel for a period of 5 days or longer, forming aggregates of the kidney cells during the cultivation period, then cultivating the kidney cells in a state of having formed aggregates, during a portion of the period, and thereby restoring the physiological functions of the kidney cells.

12 Claims, 14 Drawing Sheets

(56) References Cited

OTHER PUBLICATIONS

Lewis et al.; Pexicrine Effects of Basement Membrane Components on Paracrine Signaling by Renal Tubular Cells; Kidney International; 1996; vol. 49; pp. 48-58; International Society of Nephrology.
International Search Report based on Application No. PCT/JP2018/011392; mailed Jun. 19, 2018.
Written Opinion of the International Preliminary Examining Authority based on Application No. PCT/JP2018/011392; mailed May 7, 2019.
Written Opinion of the Internation Searching Authority based on Application No. PCT/JP2018/011392; mailed Jun. 19, 2018.
International Preliminary Report on Patentability based on Application No. PCT/JP2018/011392; mailed Jun. 27, 2019.
International Search Report based on Application No. PCT/JP2019/011389; mailed Jun. 18, 2019.
Written Opinion of the International Searching Authority based on Application No. PCT/JP2019/011389; mailed Jun. 18, 2019.
Supplemental European Search Report mailed Nov. 11, 2020 in EP Application No. 18780473.7 (9 pages).
Office Action mailed Mar. 3, 2022 in EP Application No. 18 780 473.7, 8 pages.
European Office Action dated Oct. 4, 2023 in Application No. 18780473.7 is attached, 6 pages.
U.S. Office Action dated Oct. 23, 2023 in U.S. Appl. No. 17/006,138 is attached, 12 pages.
Fok et al., ShearControlled SingleStep Mouse Embryonic Cell Expansion and Embryoid Body-Based Differentiation, Aug. 4, 2005, 11.
Office Action mailed Apr. 25, 2024 issued in co-pending U.S. Appl. No. 17/006,138.

* cited by examiner

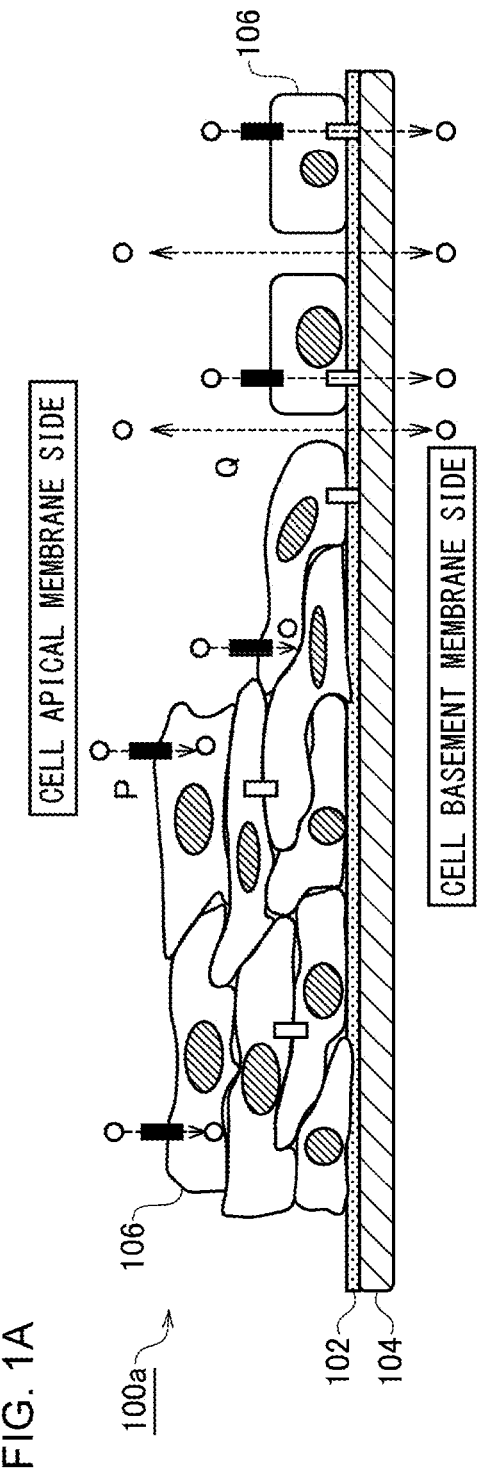
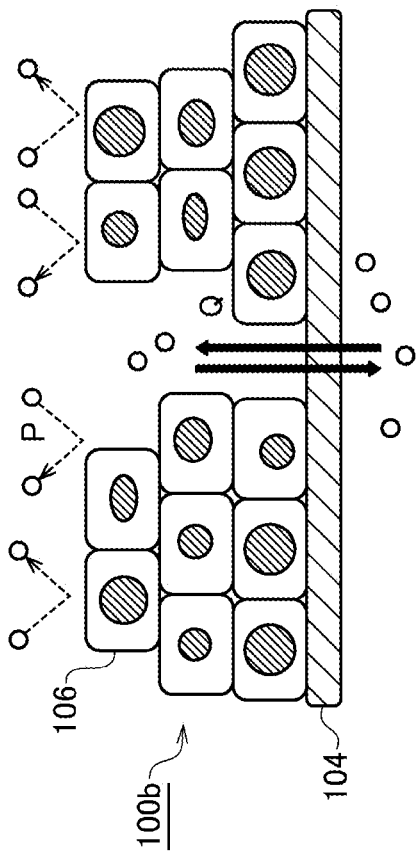
FIG. 1A
FIG. 1B

FIG. 5

| gene | Acronym | day4/day0 |
|---|---|---|
| aquaporin 1 | AQP1 | 0.412 |
| alanyl aminopeptidase | CD13 | 0.039 |
| sodium glucose cotransporter 2 | SGLT2 | 0.003 |
| $Na^+/K^+$ ATPase | Na/K ATPase | 0.138 |
| peptide transporter 1 | PEPT1 | 0.465 |
| multiple drug resistance 1 | MDR1 | 0.325 |
| organic anion transporter 1 | OAT1 | 0.208 |
| organic cation transporter novel 1 | OCTN2 | 0.031 |
| E-cadherin | E-cadherin | 0.005 |
| zonula occludens-1 | ZO-1 | 0.176 |

FIG. 6A
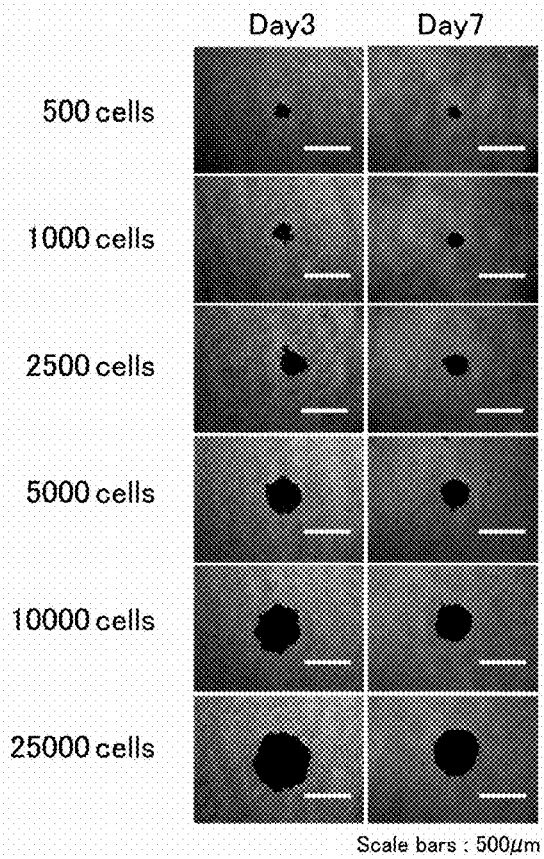
Scale bars : 500μm
FIG. 6B
| NUMBER OF SEEDED CELLS (CELLS) | MAXIMUM (μm) | MINIMUM (μm) |
|---|---|---|
| 500 | 178 | 100 |
| 1000 | 217 | 152 |
| 2500 | 296 | 217 |
| 5000 | 348 | 261 |
| 10000 | 478 | 370 |
| 25000 | 609 | 457 |
FIG. 6C
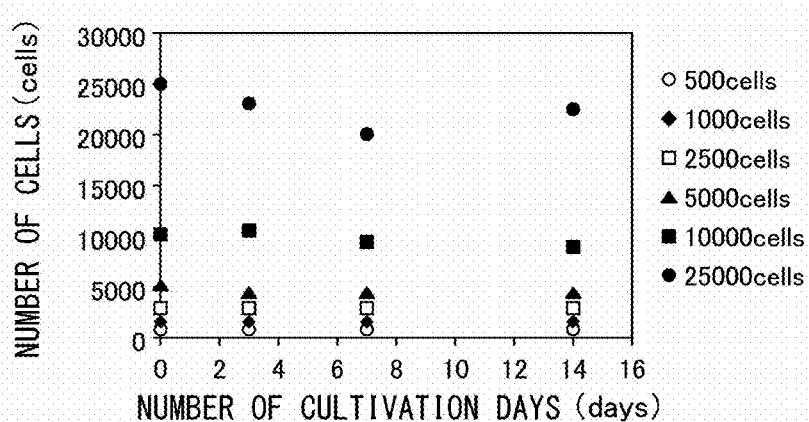

FIG. 7

| GENE | | NUMBER OF SEEDED CELLS | NUMBER OF CULTIVATION DAYS (day) | |
|---|---|---|---|---|
| | | | 3 | 7 |
| | AQP1 | 500 | 11.5 | 7.4 |
| | | 1000 | 10.7 | 8.3 |
| | | 2500 | 8.9 | 8.8 |
| | | 5000 | 0.6 | 5.6 |
| | | 10000 | 0.8 | 1.7 |
| | | 25000 | 0.1 | 0.4 |
| | | COMPARATIVE EXAMPLE | 0.01 | 0.2 |
| | SGLT2 | 500 | 33.4 | 68.3 |
| | | 1000 | 32.7 | 73.2 |
| | | 2500 | 25.9 | 66.7 |
| | | 5000 | 26.3 | 60.2 |
| | | 10000 | 23.9 | 59.0 |
| | | 25000 | 18.7 | 59.8 |
| | | COMPARATIVE EXAMPLE | 1.6 | 18.2 |
| | OAT1 | 500 | 1.1 | 503000.0 |
| | | 1000 | 1.0 | 761000.0 |
| | | 2500 | 1.8 | 100000.0 |
| | | 5000 | 1.9 | 112000.0 |
| | | 10000 | 2.3 | 31800.0 |
| | | 25000 | 1.5 | 279.0 |
| | | COMPARATIVE EXAMPLE | 16.4 | 473.2 |

FIG. 8

| GENE | NUMBER OF SEEDED CELLS | NUMBER OF CULTIVATION DAYS (day) | | | | | | | | | |
|---|---|---|---|---|---|---|---|---|---|---|---|
| | | 3 | 4 | 5 | 6 | 7 | 8 | 10 | 12 | 14 |
| AQP1 | 1000 | 5.9 | 4.6 | 10.2 | 14.8 | 19.2 | 31.6 | 35.7 | 7.3 | 13.3 |
| SGLT2 | | 65.0 | 99.5 | 116.5 | 131.9 | 230.0 | 225.1 | 382.8 | 484.9 | 641.1 |
| OAT1 | | 2.2 | 1.2 | 98355.0 | 368105.3 | 1260000.0 | 1065602.1 | 1743202.4 | 921018.6 | 2526111.1 | even# CELL CULTIVATION METHOD, CELL SUPPORT COMPOSITE PRODUCTION METHOD, CULTIVATED CELLS, AND CELL SUPPORT COMPOSITE

CROSS-REFERENCE TO RELATED APPLICATIONS

This application is based upon and claims the benefit of priority from the prior Japanese Patent Application No. 2017-075828, filed on Apr. 6, 2017, and International Patent Application No. PCT/JP2018/011392, filed on Mar. 22, 2018, the entire content of each of which is incorporated herein by reference.

BACKGROUND

Field of the Invention

The present invention relates to a cell cultivation method, a method for producing a cell support composite, cultivated cells, and a cell support composite.

Description of the Related Art

In recent years, as bio-artificial kidneys for substituting the renal functions of renal failure patients, development of modules in which a polymer membrane such as a hollow fiber membrane and kidney cells (cells having renal functions) such as renal proximal tubular epithelial cells are hybridized is in progress. Particularly, when the production, supply, and use of bio-artificial kidneys are considered, there is a need for bio-artificial kidneys that can maintain renal functions over several weeks or longer.

Furthermore, a medicine administered into a living body is discharged, after acting in the living body, from the blood into the urine at the renal proximal tubule. Therefore, renal proximal tubular cells are susceptible to the influence of medicines, and there is a possibility that the cells may be damaged by the toxicity of medicines. Therefore, in the development of new drugs, development of a module for predicting the toxicity of candidate substances to renal proximal tubular cells and for predicting the metabolism of drugs is very useful. The above-mentioned hybrid modules of a polymer membrane and renal tubular epithelial cells can also be suitably employed as this drug evaluation module.

In regard to the renal proximal tubular epithelial cells used for bio-artificial kidneys and drug evaluation modules, patent document 1 discloses a cultivation technology of prolonging the replicative senescence of renal proximal tubular epithelial cells so as to obtain a sufficient number of the cells, by suppressing gene expression of the cell cycle control factors.

patent document 1: JP2011-50358A

The inventors of the present invention repeatedly conducted thorough investigations on the cultivation technology for kidney cells such as renal proximal tubular epithelial cells, and the inventors found that in conventional cultivation technologies, the physiological functions of kidney cells are deteriorated by cultivation, and therefore, it is difficult to produce cultivated cells that can be utilized for bio-artificial kidneys or drug evaluation modules.

SUMMARY OF THE INVENTION

The present invention was made in view of such circumstances, and one of the objects of the invention is to provide a technology for obtaining cells in a state of exhibiting more satisfactory physiological functions, through cultivation.

In order to solve the problems described above, an embodiment of the present invention is a cell cultivation method. This cultivation method includes cultivating kidney cells in a state of being non-adherent to a culture vessel for a period of 5 days or longer, forming aggregates of kidney cells during the cultivation period, and then cultivating kidney cells in a state of having formed aggregates, during a portion of the period.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIG. 1A and FIG. 1B are diagrams schematically illustrating the structure of a cell support composite related to Reference Examples.

FIG. 5 is a diagram illustrating the changes over time in the amount of gene expression in a case in which cells are adherently cultivated.

FIG. 6A is a set of optical microscopic images of cells obtained on days 3 and 7 of non-adherent cultivation. FIG. 6B is a diagram showing the maximum values and the minimum values of the diameter of aggregates. FIG. 6C is a diagram showing the changes over time in the number of constituent cells of the aggregates.

FIG. 7 is a diagram showing the changes over time in the amount of gene expression in the cells constituting the aggregates.

FIG. 8 is a diagram showing the changes over time in the amount of gene expression in the cells constituting the aggregates.

DETAILED DESCRIPTION OF THE INVENTION

Figure 2A:
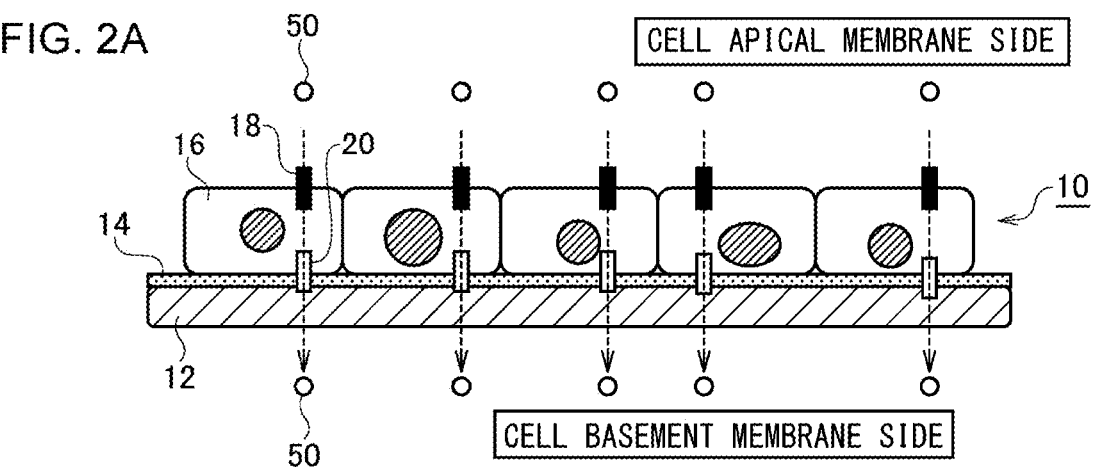
FIG. 2A to FIG. 2C are diagrams schematically illustrating the cultivated cells related to an embodiment and the configuration of a cell support composite including these cultivated cells.

An embodiment of the present invention is a cell cultivation method. This cultivation method includes cultivating kidney cells in a state of being non-adherent to a culture vessel for a period of 5 days or longer, forming aggregates of kidney cells during the cultivation period, and then cultivating kidney cells in a state of having formed aggregates, during a portion of the period. According to this embodiment, cells in a state of exhibiting more satisfactory physiological functions can be obtained.

According to the embodiment described above, the aggregates are formed on the first day of cultivation, and the cultivation period for kidney cells may be 10 days or shorter. Furthermore, the number of kidney cells constituting the aggregates may be from 500 cells to 5,000 cells. The size of the aggregates may be from 100 μm to 350 μm. The culture vessel may have been subjected to a non-cell adhesion treatment, or may be formed from a non-cell adhesive material. Furthermore, the embodiment may include cultivation of kidney cells in a medium containing collagen I. The concentration of collagen I in the medium may be more than 0.0005 mg/ml and less than 0.15 mg/ml.

Another embodiment of the present invention is a method for producing a cell support composite. This production method includes: applying a coating agent containing one or more selected from the group consisting of laminin molecules, a basement membrane matrix mixture, collagen molecules, and fragments of any of these, on at least a portion of a substrate; separating aggregates formed by the cell cultivation method of any one of the above-described embodiments into individual cultivated cells; and seeding the cultivated cells onto the substrate coated with the coating agent, cultivating the cultivated cells on the substrate, and thereby forming a single layer structure of the cultivated cells.

Still another embodiment of the present invention is cultivated cells. These cultivated cells are produced by cultivating kidney cells in a state of being non-adherent to a culture vessel for a period of 5 days or longer, forming aggregates of kidney cells during the cultivation period, and then cultivating kidney cells in a state of having formed aggregates, during a portion of the period.

Still another embodiment of the present invention is a cell support composite. This cell support composite includes a substrate; a coating agent layer covering at least a portion of the substrate, the coating agent layer containing one or more selected from the group consisting of laminin molecules, a basement membrane matrix mixture, collagen molecules, and fragments of any of these; and cultivated cells of the above-described embodiment, the cultivated cells adhering to the substrate with the coating agent layer being interposed therebetween.

In addition, any combination of the above-described constituent elements, and combinations in which the constituent elements and expressions of the present invention have been substituted with one another between methods, apparatuses, systems, and the like, are also effective as embodiments of the present invention.

The inventors of the present invention contemplated on the cultivation technologies for kidney cells and obtained the following recognition. That is, kidney cells such as renal proximal tubular epithelial cells isolated from the kidney by an enzyme treatment (primary cultured cells) are dedifferentiated by elimination of the in-vivo environment or by a culture environment such as two-dimensional culture on a Petri dish, and the functions are gradually lost. For this reason, only by simply cultivating kidney cells, cells having insufficient physiological functions merely increase. In a case in which a bio-artificial kidney is produced using dedifferentiated cells, there is a possibility that the function of reabsorbing useful components in the blood plasma may not be sufficiently high. Furthermore, in a case in which a drug evaluation module is produced using dedifferentiated cells, there is a possibility that the drug evaluation module may not exhibit pharmacokinetics or toxic response with high accuracy. In this regard, the inventors of the present invention found that when particular cultivation is carried out, the physiological functions of dedifferentiated kidney cells are restored.

Furthermore, the renal proximal tubular epithelial cells isolated from the kidney cannot maintain the original columnar cell structure and change into a flat shape. Moreover, when the renal proximal tubular epithelial cells are seeded on a Petri dish or an artificial membrane, the single layer epithelial structure is lost, and gaps are generated between the cells, or the cells become multilayered. As such a phenomenon occurs, the function of reabsorbing useful components in a bio-artificial kidney may be deteriorated. Also, the accuracy of the drug evaluation module may be decreased. In this regard, the inventors of the present invention found a technology for forming a stable single layer epithelial structure on a substrate using renal proximal tubular epithelial cells that have restored physiological functions. Embodiments have been devised on the basis of such speculation.

In the following description, the present invention will be explained on the basis of suitable embodiments with reference to the drawings. The embodiments are not intended to limit the invention and are only for illustrative purpose. All the features and combinations described in embodiments shall not be considered to be necessarily essential to the invention. The same or equivalent components, members, and treatments illustrated in the respective drawings will be assigned with the same reference symbols, and redundant descriptions will not be repeated as appropriate. The scale and shapes of various parts shown in the respective drawings are conveniently set for the ease of explanation, and unless particularly stated otherwise, the scale and shapes are not intended to be construed limitatively. Furthermore, in a case in which terms such as "first" and "second" are used in the present specification or claims, these terms are not intended to represent any order or importance, but are used in order to distinguish a certain configuration from another configuration.

FIG. 1A and FIG. 1B are diagrams schematically illustrating the structure of a cell support composite related to Reference Example. In FIG. 1A, a cell support composite obtainable in the case of using a general coating agent is illustrated. In FIG. 1B, a cell support composite obtainable in a case in which a coating agent is not used is illustrated. As shown in FIG. 1A, in a cell support composite 100a obtainable by seeding renal proximal tubular epithelial cells 106 on a substrate 104 such as an artificial membrane coated with a common coating agent 102 that is conventionally known, there are occasions in which the renal proximal tubular epithelial cells 106 become multilayered, or gaps are generated between the cells. As shown in FIG. 1B, also in a cell support composite 100b obtainable by seeding renal proximal tubular epithelial cells 106 on a substrate 104 that is not coated with a coating agent 102, multilayering of the renal proximal tubular epithelial cells 106 or generation of gaps occurred similarly.

In a region in which the renal proximal tubular epithelial cells 106 have been multilayered, the migration of useful substances from the cell apical membrane side to the cell basement membrane side by means of transporters may be disturbed (arrow P). Furthermore, in the gaps of adjoining renal proximal tubular epithelial cells 106, concentration-dependent material transfer through the substrate 104 may occur (arrow Q).

Figure 2B:
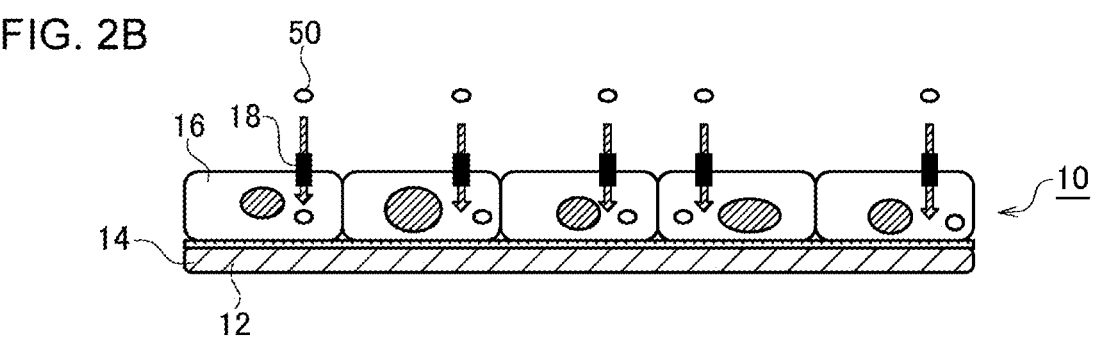
Figure 2C:
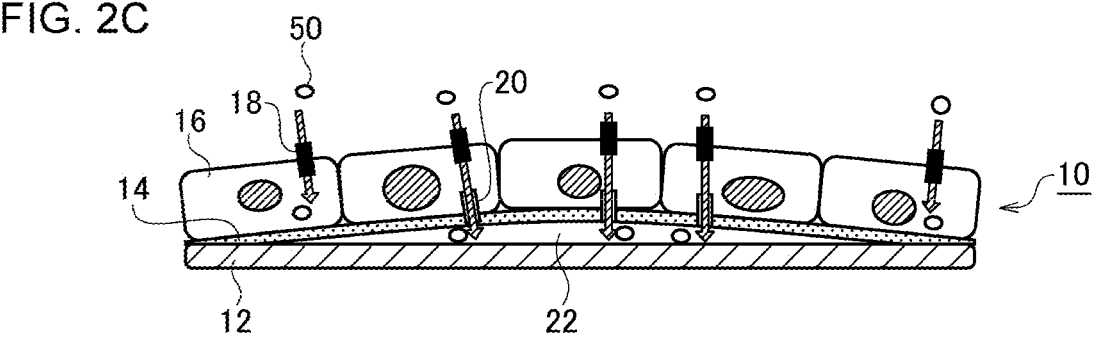

FIG. 2A to FIG. 2C are diagrams schematically illustrating the cultivated cells according to an embodiment and the configuration of a cell support composite including these cultivated cells. In FIG. 2A, a cell support composite obtainable in the case of using a substrate having water permeability, in other words, a substrate having relatively high water permeability, is illustrated. In FIG. 2B, a cell support composite obtainable in the case of using a substrate that does not have water permeability, in other words, a substrate having relatively low water permeability, in a state in which a short period of time has elapsed, is illustrated. In FIG. 2C, a cell support composite obtainable in the case of using a substrate that does not have water permeability, in a state in which a long period of time has elapsed, is illustrated.

The cell support composite 10 includes a substrate 12, a coating agent layer 14, and cultivated cells 16.

Substrate

The substrate 12 is formed from, for example, an artificial material. As shown in FIG. 2A, the substrate 12 has permeability to water and various ions. Furthermore, it is preferable that the substrate 12 has also permeability to sugars and low-molecular weight proteins. A cell support composite 10 including such a substrate 12 can be utilized as, for example, a bio-artificial kidney. A useful substance 50 present on the cell apical membrane side passes through the cell support composite 10 by means of transporters 18 on the cell apical membrane side and transporters 20 on the cell basement membrane side possessed by cultivated cells 16, and the substrate 12, and the useful substance 50 moves toward the cell basement membrane side.

In order to make the substrate 12 have permeability to various substances, the substrate 12 is provided with, for example, holes. The average hole diameter of the holes provided in the substrate 12 is preferably 5 µm or less. When the average hole diameter is adjusted to 5 µm or less, the risk of the cultivated cells 16 passing through the substrate 12 can be reduced. As such a substrate 12, for example, Transwell (Corning Inc.; average hole diameter 0.4 µm or 3.0 µm) can be used.

As illustrated in FIG. 2B and FIG. 2C, the substrate 12 may not have permeability to water and various ions. A cell support composite 10 including such a substrate 12 can be utilized as, for example, a drug evaluation module for evaluating the metabolism of a drug (amount of intake of a drug by the cultivated cells 16, or the like) or toxicity. A Petri dish, a well plate, or the like, which does not have water permeability, can be used as the substrate 12. A useful substance 50 present on the cell apical membrane side is taken in by the cultivated cells 16 by means of transporters 18 of the cultivated cells 16. During a short period of time from the initiation of use, the migration of the useful substance 50 by means of the transporters 20 of the cultivated cells 16 toward the cell basement membrane side occurs at a low level, transformation does not occur in the layer of the cultivated cells 16, as illustrated in FIG. 2B. On the other hand, when a long period of time elapses, the amount of migration of the useful substance 50 by means of transporters 20 is increased; however, since the useful substance 50 does not pass through the substrate 12, the layer of the cultivated cells 16 is lifted up as shown in FIG. 2C, and a dome 22 is formed.

The material that constitutes the substrate 12 is not particularly limited; however, examples include polystyrene, polycarbonate (PC), polyester (PET), a polyester-based polymer alloy (PEPA), an ethylene-vinyl alcohol copolymer (EVOH), polyethylene, polysulfone (PSf), and polyethersulfone (PES). Furthermore, the form of the substrate 12 is not particularly limited; however, examples include a culture well plate, a culture Petri dish; artificial membranes such as a hollow fiber membrane, a Transwell, and a flat membrane; a micro flow channel chip, solid particles, and hollow particles.

Coating Agent Layer

The coating agent layer 14 is a layer formed from a coating agent. The coating agent layer 14 covers at least a portion of the substrate 12. The coating agent layer 14 is adhered to the surface of the substrate 12 and is fixed to the substrate 12. The phrase "at least a portion of the substrate 12" means, for example, at least one surface of a substrate 12 having a flat surface or a curved surface. In a case in which the substrate 12 has a flat shape, the "at least a portion of the substrate 12" means, for example, at least one of the principal surfaces of a flat plate. In a case in which the substrate 12 has a cylindrical shape, the "at least a portion of the substrate 12" means, for example, at least one of the inner surface or the outer surface of a cylinder.

The coating agent contains one or more adhesive molecules selected from the group consisting of laminin molecules, a basement membrane matrix mixture, collagen molecules, and fragments of any of these. As the coating agent layer 14 contains these adhesive molecules, a single layer structure of the cultivated cells 16 can be formed more reliably.

Laminin Molecules

A laminin molecule adopts a hetero-trimer structure having one each of an α-chain, a β-chain, and a γ-chain. At present, five kinds of α-chins, three kinds of β-chains, and three kinds of γ-chains have been identified. Laminin molecules are known to form at least 12 kinds of isoforms through combinations of these. In the present embodiment, the laminin molecule is selected from one or more of laminin 111, laminin 211, laminin 221, laminin 311, laminin 332, laminin 421, laminin 511, laminin 521, and fragments of these.

Laminin molecules include modified bodies of laminins (modified laminins) obtained by adding predetermined modifying groups into one or more sites of the above-mentioned isoforms. The modified bodies also include gene recombinants, that is, proteins obtained by introducing mutation into proteins obtained from recombinant genes, partial proteins of gene recombinants, and proteins having gene recombinant-derived peptides.

Among the isoforms of laminin molecules, laminin 311, laminin 511, and laminin 521 are more preferred because the values of electric resistance, which is an index of the intercellular barrier function, are higher than that of laminin 111. Furthermore, laminin 511 and laminin 521 are more preferred because the cost is cheaper compared to, for example, laminin 111.

The concentration of a laminin molecule in the coating agent and the amount of adhesion of a laminin molecule to the substrate 12 are adjusted as appropriate so that the cell support composite 10 can maintain its functions during the period of actual use. The amount of adhesion of a laminin molecule can be controlled by adjusting the concentration of the laminin molecule in the coating agent. The period of actual use of the cell support composite 10 is preferably two or more weeks, more preferably three or more weeks, and even more preferably four or more weeks, from the initiation of cultivation of the cultivated cells 16 on the substrate 12.

The amount of adhesion of a laminin molecule to the substrate 12 can be measured using a method that is known to those ordinarily skilled in the art. For example, when a coating agent containing a laminin molecule is applied on a substrate 12, and then the coating agent is left to stand overnight at 4° C., a coating agent layer 14 is formed. Then, the amount of the laminin molecule adhered to the substrate 12 is quantitatively determined using, for example, a 2-D Quant Kit (GE Healthcare Corp.).

In the case of laminin 111, it is preferable that the concentration is adjusted to be 3.0 μd g/ml or higher, and thereby the amount of adhesion is adjusted to be about 0.15 $\mu g/cm^2$ or greater. Accordingly, the functions as an adhesive molecule can be exhibited more reliably. Furthermore, a single layer structure of the cultivated cells 16 can be maintained for about 15 days or longer. It is more preferable that the concentration is adjusted to be 4.0 μg/ml or higher, and thereby the amount of adhesion is adjusted to be about 0.19 $\mu g/cm^2$ or greater. Accordingly, a single layer structure of the cultivated cells 16 can be maintained for 28 days or longer.

In the case of laminin 211, it is preferable that the concentration is adjusted to be higher than 8.0 μg/ml, and thereby the amount of adhesion is adjusted to be greater than about 0.45 $\mu g/cm^2$. Accordingly, the functions as an adhesive molecule can be exhibited more reliably. Furthermore, a single layer structure of the cultivated cells 16 can be maintained for about 15 days or longer. Furthermore, it is more preferable that the concentration is adjusted to be 10 μg/ml or higher, and thereby the amount of adhesion is adjusted to be about 0.52 $\mu g/cm^2$ or greater. Accordingly, a single layer structure of the cultivated cells 16 can be maintained for 28 days or longer.

In the case of laminin 221, it is preferable that the concentration is adjusted to be higher than 8.0 μg/ml, and thereby the amount of adhesion is adjusted to be greater than about 0.30 $\mu g/cm^2$. Accordingly, the functions as an adhesive molecule can be exhibited more reliably. Furthermore, a single layer structure of the cultivated cells 16 can be maintained for about 15 days or longer. Furthermore, it is more preferable that the concentration is adjusted to be 10 μg/ml or higher, and thereby the amount of adhesion is adjusted to be about 0.34 $\mu g/cm^2$ or greater. Accordingly, a single layer structure of the cultivated cells 16 can be maintained for 18 days or longer.

In the case of laminin 311, it is preferable that the concentration is adjusted to be about 2.5 μg/ml or higher, and thereby the amount of adhesion is adjusted to be about 0.10 $\mu g/cm^2$ or greater. Accordingly, the functions as an adhesive molecule can be exhibited more reliably. Furthermore, a single layer structure of the cultivated cells 16 can be maintained for 15 days or longer. Furthermore, it is more preferable that the concentration is adjusted to be 4.0 μg/ml or higher, and thereby the amount of adhesion is adjusted to be about 0.15 $\mu g/cm^2$ or greater. Accordingly, a single layer structure of the cultivated cells 16 can be maintained for 28 days or longer.

In the case of laminin 332, it is preferable that the concentration is adjusted to be 8.0 μg/ml or higher. Accordingly, the functions as an adhesive molecule can be exhibited more reliably. Furthermore, a single layer structure of the cultivated cells 16 can be maintained for 15 days or longer. Furthermore, it is more preferable that the concentration is adjusted to be 10 μg/ml or higher. Accordingly, a single layer structure of the cultivated cells 16 can be maintained to be 18 days or longer.

In the case of laminin 421, it is preferable that the concentration is adjusted to be 5.0 μg/ml or higher, and thereby the amount of adhesion is adjusted to be about 0.50 $\mu g/cm^2$ or higher. Accordingly, the functions as an adhesive molecule can be exhibited more reliably. Furthermore, a single layer structure of the cultivated cells 16 can be maintained for 15 days or longer. Furthermore, it is more preferable that the concentration is adjusted to be 6.0 μg/ml or higher, and thereby the amount of adhesion is adjusted to be about 0.54 $\mu g/cm^2$ or greater. Accordingly, a single layer structure of the cultivated cells 16 can be maintained for 18 days or longer. Furthermore, it is even more preferable that the concentration is adjusted to be 10 μg/ml or higher, and thereby the amount of adhesion is adjusted to be about 0.69 $\mu g/cm^2$ or greater. Accordingly, a single layer structure of the cultivated cells 16 can be maintained for 28 days or longer.

In the case of laminin 511, it is preferable that the concentration is adjusted to be higher than about 8.0 μg/ml, and thereby the amount of adhesion is adjusted to be greater than about 0.30 $\mu g/cm^2$. Accordingly, the functions as an adhesive molecule can be exhibited more reliably. Furthermore, a single layer structure of the cultivated cells 16 can be maintained for about 15 days or longer. Furthermore, it is more preferable that the concentration is adjusted to be 10 μg/ml or higher, and thereby the amount of adhesion is adjusted to be about 0.32 $\mu g/cm^2$ or greater. Accordingly, a single layer structure of the cultivated cells 16 can be maintained for 18 days or longer.

In the case of laminin 521, it is preferable that the concentration is adjusted to be about 4.5 μg/ml or higher, and thereby the amount of adhesion is adjusted to be about 0.40 $\mu g/cm^2$ or greater. Accordingly, the functions as an adhesive molecule can be exhibited more reliably. Furthermore, a single layer structure of the cultivated cells 16 can be maintained for about 15 days or longer. It is more preferable that the concentration is adjusted to be 5.0 μg/ml or higher, and thereby the amount of adhesion is adjusted to 0.44 $\mu g/cm^2$ or greater. Accordingly, a single layer structure of the cultivated cells 16 can be maintained for 28 days or longer.

Meanwhile, when the concentrations of commercially available products of various laminin molecules are taken into consideration, the treatment becomes complicated at a concentration of higher than 100 μg/ml, and large cost is needed. Therefore, it is preferable that the concentrations of the respective laminin molecules are 100 μg/ml or less.

In a case in which a modified laminin is used as the laminin molecule, the modifying group is, for example, a growth factor binding molecule or a cell adhesive molecule. Even in a case in which such a modified laminin is used, an operating effect similar to that of an unmodified laminin molecule can be provided.

A fragment of a laminin molecule may also be used as an adhesive factor to be incorporated into the coating agent. An example of the fragment of a laminin molecule is a modified body of the E8 region including a cell adhesive site (integrin-binding site) of domain I in a full-length laminin (described as laminin***-E8). Examples of such a modified body include laminin 111-E8, laminin 211-E8, laminin 421-E8, and laminin 521-E8. The molecular weights of these are all about ⅕ of full-length laminin.

In a case in which a modified body of the E8 region of laminin 511 (laminin 511-E8) is used as a fragment of a laminin molecule, when the concentration of commercially available laminin 511-E8 (iMatrix-511; Nippi, Inc.) is considered, it is preferable that the concentration is adjusted to be from about 1.4 µg/ml to about 500 µg/ml, and thereby the amount of adhesion is adjusted to be from 0.15 µg/cm$^2$ to 31.18 µg/cm$^2$. When the concentration of laminin 511-E8 is adjusted to be about 1.4 µg/ml or higher, the functions as an adhesive molecule can be exhibited more reliably. Furthermore, when the concentration of laminin 511-E8 is adjusted to be about 500 µg/ml or less, preparation of the coating agent becoming difficult can be avoided. Thereby, a single layer structure of the cultivated cells 16 can be maintained for 28 days or longer. Furthermore, it is more preferable that the concentration is adjusted to be from about 2.5 µg/ml to about 50 µg/ml, and thereby the amount of adhesion is adjusted to be from 0.21 µg/cm$^2$ to 6.21 µg/cm$^2$.

Regarding the fragment of a laminin molecule, not only a modified body of the E8 region but also a laminin peptide having cell adhesion activity, or a product obtained by synthesizing only cell active sites into a peptide can be used. Examples of such a laminin peptide include a YIGSR-containing peptide derived from domain III of the β-chain, a PDSGR-containing peptide derived from domain III of the β-chain, an RYVVLPR-containing peptide derived from domain III of the S-chain, an RGD-containing peptide derived from domain III of the α-chain, a KAFDITYVRLKF-containing peptide derived from domain I of the γ-chain, an IKVAV-containing peptide derived from domain I of the α-chain, and an LRE-containing peptide derived from domain I of the β-chain. The concentration of the laminin peptide is, for example, about 0.5 to about 500 µg/ml. Meanwhile, the size of the fragment of a laminin molecule is not particularly limited.

In the case of using a fragment of a laminin molecule, since the molecular weight is small compared to that of a full-length laminin molecule, more stabilized coating is enabled. Furthermore, it becomes easy to perform coating in fine regions. Furthermore, since aggregation of adhesive molecules does not occur easily, formation of uneven coating can be suppressed. Thereby, the single layer structure of the cultivated cells 16 becoming non-uniform can be suppressed. By using a fragment of a laminin molecule, adhesive molecules can be coated at a high concentration and a high density. Moreover, for a recombinant protein, as the molecular weight is smaller, the production efficiency and the purification efficiency are increased. Therefore, the production cost for the cell support composite 10 can be further reduced by using a fragment of a laminin molecule.

The full-length laminin molecule and the fragment of a laminin molecule may be each used as a mixture of a plurality of isoforms. Furthermore, it is also acceptable that a full-length laminin molecule and a fragment of a laminin molecule may be used as a mixture. It is also acceptable that a plurality of coating agents each containing different kinds of full-length laminins and/or fragments of laminin molecules is applied on a substrate 12, and thereby a plurality of coating agent layers 14 containing different kinds of laminins is laminated.

Basement Membrane Matrix Mixture

The basement membrane matrix mixture is a mixture of extracellular matrix proteins extracted from mouse sarcoma. The basement membrane matrix mixture includes laminins, collagen IV, and entactin as main constituent components. An example of the basement membrane matrix mixture is a soluble basement membrane matrix extracted from Engelbreth-Holm-Swarm (EHS) mouse sarcoma (MATRIGEL®, registered trademark; Corning Inc.).

MATRIGEL® is rich in extracellular matrix proteins. In the present embodiment, MATRIGEL® also includes, in addition to conventional MATRIGEL® containing growth factors, a MATRIGEL® containing a reduced amount of growth factors (Growth Factor Reduced MATRIGEL® Matrix) compared to the foregoing MATRIGEL®. In the following description, as appropriate, conventional MATRIGEL® is referred to as first MATRIGEL®, and a growth factor-reduced MATRIGEL® is referred to as second MATRIGEL®. The first MATRIGEL® and second MATRIGEL® can be purchased from, for example, Corning Inc. The first MATRIGEL® includes about 56% of laminins, about 31% of collagen IV, and about 8% of entactin. On the other hand, the second MATRIGEL® includes about 61% of laminins, about 30% of collagen IV, and about 7% of entactin.

Regarding the basement membrane matrix mixture, a mixture in which laminins, collagen IV, and entactin are mixed at a mass ratio of about 56 to about 61:about 30 to about 31 about 7 to about 8, can also be used.

The concentration of the basement membrane matrix mixture in the coating agent and the amount of adhesion of the basement membrane matrix mixture to the substrate 12 are appropriately adjusted so that the cell support composite 10 can maintain the performance during the period of actual use. The amount of adhesion of the basement membrane matrix mixture can be controlled by adjusting the concentration of the basement membrane matrix mixture in the coating agent.

In the case of the first MATRIGEL®, it is preferable that the concentration is adjusted to be higher than 0 µg/ml and 3,000 µg/ml or lower, and thereby the amount of adhesion is adjusted to be greater than 0 µg/cm$^2$ and about 34.85 µg/cm$^2$ or less. By adjusting the concentration of the first MATRIGEL® to be 3,000 µg/ml or lower, the risk that the first MATRIGEL® is gelated to cause the cultivated cells 16 to aggregate can be reduced. Furthermore, it is more preferable that the concentration is adjusted to from 5.0 µg/ml to 2,000 µg/ml, and thereby the amount of adhesion is adjusted to be from about 0.5 µg/cm$^2$ to about 25 µg/cm$^2$. Furthermore, it is even more preferable that the concentration is adjusted to be from 5.0 µg/ml to 1,000 µg/ml, and thereby the amount of adhesion is adjusted to be from about 0.5 µg/cm$^2$ to about 16.04 µg/cm$^2$. Accordingly, a single layer structure of the cultivated cells 16 can be maintained for 28 days or longer.

In the case of the second MATRIGEL®, it is preferable that the concentration is adjusted to be higher than 20 µg/ml and 1,000 µg/ml or lower, and thereby the amount of adhesion is adjusted to be greater than 1.36 µg/cm$^2$ and 30.6 µg/cm$^2$ or less. When the concentration of the second MATRIGEL® is adjusted to be higher than 20 µg/ml, the functions as an adhesive molecule can be exhibited more reliably. Furthermore, by adjusting the concentration of the second MATRIGEL® to be 1,000 µg/ml or lower, the risk that the second MATRIGEL® is gelated to cause aggregation of the cultivated cells 16 can be reduced. It is more preferable that the concentration is adjusted to be from 40 µg/ml to 1,000 µg/ml, and thereby the amount of adhesion is adjusted to be from 3.15 µg/cm$^2$ to 30.6 µg/cm$^2$. Accordingly, a single layer structure of the cultivated cells 16 can be maintained for 28 days or longer.

As the adhesive factor to be incorporated into the coating agent, a fragment of the basement membrane matrix mixture may be used. A fragment of a basement membrane matrix mixture means a mixture of at least one of a fragment of a laminin, a fragment of collagen IV, and a fragment of entactin. Furthermore, it is also acceptable that a mixture of a plurality of kinds of the whole bodies of basement membrane matrix mixtures and a mixture of a plurality of kinds of the fragments thereof may also be each used. It is also acceptable that a mixture of the whole bodies and fragments is used. Furthermore, a plurality of coating agents containing different kinds of whole bodies and/or fragments may be applied on a substrate 12, and thereby a plurality of coating agent layers 14 containing different kinds of mixtures may be laminated.

Collagen Molecules

Examples of collagen molecules include collagen I and collagen IV. These can be purchased from, for example, Nitta Gelatin Inc. The concentration of collagen molecules in the coating agent and the amount of adhesion of collagen molecules to the substrate 12 are appropriately adjusted so that the cell support composite 10 can maintain its performance during the period of actual use. The amount of adhesion of the collagen molecules can be controlled by adjusting the concentration of the collagen molecules in the coating agent.

In the case of collagen I, it is preferable that the concentration is adjusted to be higher than 750 µg/ml and 3,000 µg/ml or lower, and thereby the amount of adhesion is adjusted to be greater than about 50 µg/cm$^2$ and 138 µg/cm$^2$ or less. By adjusting the concentration of collagen I to be higher than 750 µg/ml, the functions as an adhesive molecule can be exhibited more reliably. Furthermore, by adjusting the concentration of collagen I to be adjusted to 3,000 µg/ml or lower, uniform application of the coating agent becoming difficult due to the high viscosity of collagen I, can be avoided more reliably. Accordingly, a single layer structure of the cultivated cells 16 can be maintained for 15 days or longer. Furthermore, it is more preferable that the concentration is adjusted to be from 1,000 µg/ml to 3,000 µg/ml, and thereby the amount of adhesion is adjusted to be from 65.4 µg/cm$^2$ to 138 µg/cm$^2$. Accordingly, a single layer structure of the cultivated cells 16 can be maintained for 28 days or longer.

In the case of collagen IV, it is preferable that the concentration is adjusted to be higher than 500 µg/ml and 3,000 µg/ml or lower, and thereby the amount of adhesion is adjusted to be greater than 19.2 µg/cm$^2$ and 121 µg/cm$^2$ or less. By adjusting the concentration of collagen IV to be higher than 500 µg/ml, the functions as an adhesive molecule can be exhibited more reliably. Furthermore, by adjusting the concentration of collagen IV to be 3,000 µg/ml or lower, uniform application of the coating agent becoming difficult due to the high viscosity of collagen IV, can be avoided more reliably. Accordingly, a single layer of the cultivated cells 16 can be maintained for 15 days or longer. Furthermore, it is more preferable that the concentration is adjusted to be from 750 µg/ml to 3,000 µg/ml, and thereby the amount of adhesion is adjusted to be from about 25 µg/cm$^2$ to 121 µg/cm$^2$. Accordingly, a single layer structure of the cultivated cells 16 can be maintained for 28 days or longer.

As the adhesive factor to be incorporated into the coating agent, a fragment of a collagen molecule may be used. Furthermore, it is also acceptable that a mixture of a plurality of kinds of the whole bodies of collagen molecules and a mixture of a plurality of kinds of the fragments thereof may also be each used. It is also acceptable that a mixture of the whole bodies and fragments is used. Furthermore, a plurality of coating agents containing different kinds of whole bodies and/or fragments may be applied on a substrate 12, and thereby a plurality of coating agent layers 14 containing different kinds of collagens may be laminated.

The above-mentioned laminin molecules, basement membrane matrix mixture, collagen molecules, and fragments of these may be each used singly, or two or more kinds thereof may be used as a mixture. In the coating agent, other adhesive proteins such as gelatin may be further incorporated.

Cultivated Cells

The cultivated cells 16 adhere to the substrate 12, with the coating agent layer 14 being interposed therebetween. That is, the cultivated cells 16 are fixed to the substrate 12 by means of the coating agent layer 14. The cultivated cells 16 have transporters 18 that are positioned on the cell apical membrane side, and transporters 20 that are positioned on the cell basement membrane side.

The cultivated cells 16 are produced by cultivating kidney cells in a state of being non-adherent to a culture vessel for 5 days or longer (that is, 120 hours or longer). The cultivated cells 16 need to maintain physiological functions in order to be used in a cell support composite 10. On the other hand, when kidney cells are cultivated in an environment different from an in-vivo environment, the kidney cells are dedifferentiated, and physiological functions are deteriorated. In contrast, when kidney cells are cultivated in a state of being non-adherent to a culture vessel for 5 days or longer, the deteriorated physiological functions of kidney cells can be restored. Meanwhile, when deteriorated physiological functions are even slightly improved by cultivation, this occurrence is also included in the term "restoration" according to the present embodiment.

More specifically, when kidney cells are cultivated in a state of being non-adherent to a culture vessel, the kidney cells form aggregates during the cultivation period. For example, aggregates of kidney cells are formed on the first day of cultivation (that is, within 24 hours). When kidney cells are cultivated in a state of having formed aggregates for a portion of the period, the physiological functions of kidney cells can be restored. Therefore, the cultivated cells 16 are cells having the physiological functions of kidney cells. The method for cultivating cells will be explained in detail below.

Kidney cells constituting the cultivated cells 16 include tissue-derived kidney cells, and iPS cell- or ES cell-derived kidney cells. Furthermore, kidney cells include, for example, at least one of the epithelial cells of a renal proximal tubule system, a renal distal tubule system, and a collecting tubule system. More specifically, examples of the kidney cells include human renal proximal tubular epithelial cells, human renal distal tubular epithelial cells, and human collecting tubular epithelial cells collected and isolated from the kidney; and renal proximal tubular epithelial cells, renal distal tubular epithelial cells, and collecting tubular epithelial cells differentiation-induced from human iPS cells or human ES cells. More preferably, the kidney cells are renal proximal tubular epithelial cells. Furthermore, the kidney cells include immortalized cells and established cell lines (HK-2 cells and the like) of the above-mentioned kidney cells, and transformed cells obtained by introducing a gene into kidney cells in order to express a protein such as a particular transporter. In addition, as the kidney cells, cells derived from other animal species (MDCK cells, LLC-PK1 cells, JTC-12 cells, and the like) can also be used in place of human-derived kidney cells.

The cultivated cells 16 form a confluent single layer on the substrate 12 without substantial multilayering. The term "substantially" means that the single layer structure is maintained to the extent that a decrease in the migration efficiency of substances caused by multilayering does not cause a problem, and it is not necessarily meant that multilayering does not at all occurs. Furthermore, the term "confluent" means a state in which the proportion of area occupied by cells with respect to the entire culture surface of the cultivated cells 16 is 100%, that is, cells have proliferated fully over the culture surface without any gaps. Whether cells are in a confluent state can be easily determined by those ordinarily skilled in the art.

Cell Cultivation Method and Method for Producing Cell Support Composite

FIG. 3A to FIG. 3E are process diagrams for a cell cultivation method and a method for producing a cell support composite according to embodiments. The cell cultivation method according to the present embodiment includes cultivating the above-mentioned kidney cells in a state of being non-adherent to a culture vessel for a period of 5 days or longer, forming aggregates during the cultivation period, and then cultivating the kidney cells in a state of having formed aggregates, for a portion of the period. Through this cultivation method, cultivated cells 16 in a state of exhibiting physiological functions can be produced.

The method for producing a cell support composite according to the present embodiment includes: applying a coating agent on at least a portion of a substrate 12; separating aggregates 30 of cultivated cells 16 formed by the cell cultivation method according to the present embodiment into individual cultivated cells 16; and seeding the cultivated cells 16 on the substrate 12 coated with the coating agent, cultivating the cultivated cells 16 on the substrate 12, and thereby forming a single layer structure of the cultivated cells 16.

Figure 3A:
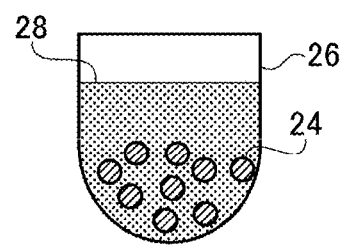
FIG. 3A to FIG. 3E are process diagrams of the cell cultivation method and the method for producing a cell support composite related to an embodiment.

Specifically, as shown in FIG. 3A, kidney cells 24 are seeded into a culture vessel 26. Examples of the culture vessel 26 include a U-bottom 96-well plate, a V-bottom 96-well plate, a U-bottom 384-well plate, a microwell plate having a larger number of wells, a spinner flask, a Petri dish, a hollow fiber, a bottle, and a micro flow channel. The number of seedings of kidney cells 24 per well of the culture vessel 26 is preferably from 500 to 5,000.

In the culture vessel 26, medium 28 is added. As the medium 28, conventionally known media, for example, REGM (Lonza Group AG), EpiCM (ScienCell Research Laboratories, Inc.), and Keratinocyte SFM (Life Technologies Corp.) can be used. Furthermore, any conventionally known materials required for cell cultivation can be used as appropriate.

Figure 3B:
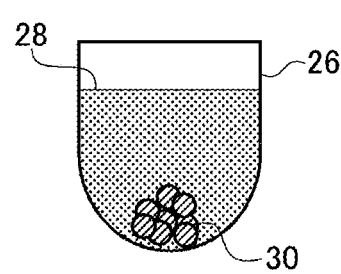

Then, the kidney cells 24 are cultivated for a period of 5 days or longer. The kidney cells 24 are cultivated in a state in which the cells are not adherent to the surface of the culture vessel 26. Therefore, as shown in FIG. 3B, aggregates 30 of the kidney cells 24 are formed during the cultivation period. By cultivating the kidney cells 24 in the form of the aggregates 30, the cultivated cells 16 that are in a state of exhibiting more satisfactory physiological functions can be obtained. The size of the aggregates 30 is, for example, from about 100 μm to about 350 μm. The size of the aggregates 30 can be controlled by adjusting the number of cells to be seeded into the culture vessel 26. The size of an aggregate 30 is defined as the largest width of the aggregate 30. That is, the size of an aggregate 30 is the length of the largest straight lines among all straight lines connecting two points on the outer periphery of the aggregate 30. In addition, since the aggregates 30 are approximately spherical in shape, in the following description, the size of the aggregates 30 will be referred to as the diameter of the aggregates 30 for convenience.

For example, in a case in which cells are cultivated on a multi-well plate, one aggregate 30 is formed in one well. Therefore, when the number of seedings of kidney cells 24 per well is from 500 to 5,000, the number of kidney cells constituting the aggregates 30 is from 500 to 5,000. The size of the aggregates 30 is from 100 μm to 350 μm when the number of constituent cells is from 500 to 5,000. By adjusting the number of constituent cells of the aggregates 30 to be 500 or more, or by adjusting the size to be 100 μm or larger, cell aggregates being suctioned together with old medium at the time of medium exchange or the like can be avoided reliably. Furthermore, by adjusting the number of constituent cells to be 5,000 or less, or by adjusting the size to be 350 μm or less, cultivated cells 16 having more satisfactory physiological functions can be obtained.

In a case in which it is wished to form more numerous aggregates 30, it is preferable to cultivate cells using a vessel such as a Petri dish or a spinner flask. In this case, the diameter of the aggregates 30, in other words, the number of kidney cells 24 that constitute one aggregate 30, can be controlled by adjusting the cell density in the vessel. For example, in a case in which aggregates 30 in which the diameter is from about 100 μm to about 350 μm, or the number of constituent cells is from 500 to 5,000, are formed on a 60-mm Petri dish (Sumitomo Bakelite Co., Ltd.), the cell density in the Petri dish is adjusted to be from 1,500 cells/cm$^2$ to 15,000 cells/cm$^2$. Then, the kidney cells 24 are subjected to stationary cultivation, shaking cultivation, or stirred cultivation, a plurality of aggregates 30 having a desired diameter or a desired number of constituent cells can be formed all at one time. Meanwhile, in a case in which kidney cells 24 are cultivated using a Petri dish or a flask, the medium exchange is carried out by collecting the entire amount of medium containing the aggregates 30, and then settling the aggregates 30 by centrifugation.

It is preferable that collagen I (Type I collagen) is added to the medium 28. Collagen I has a function of adhering kidney cells 24 to one another. Therefore, when kidney cells 24 are cultivated in a medium 28 containing collagen I, aggregates 30 can be formed more reliably. Collagen I is preferably full-length collagen I; however, collagen I may also be the α1 chain or α2 chain constituting collagen I, or a collagen peptide obtained by fragmenting the various chains. The animal species from which collagen I Is obtained is not particularly, and not only human-derived collagen I but also collagen I derived from other animals can be used.

The concentration of collagen I in the medium 28 is preferably higher than 0.0005 mg/ml and lower than 0.15 mg/ml. That is, it is preferable that collagen I is added to the medium at a concentration of higher than 0.0005 mg and lower than 0.15 mg in 1 ml of the medium (in other words, cell suspension). By adjusting the concentration of collagen I to be higher than 0.0005 mg/ml, the effect of promoting the formation of aggregates 30 by collagen I can be exhibited more reliably. Furthermore, by adjusting the concentration of collagen I to be lower than 0.15 mg/ml, the risk of collagen I gelating in the medium 28 can be avoided more reliably. As a result, the effect of promoting the formation of aggregates 30 by collagen I can be exhibited more reliably.

Furthermore, by setting the amount of collagen I to be added to the cell suspension to be in the above-described range, aggregates 30 can be caused to form more reliably within 24 hours after cell seeding.

The concentration of collagen I in the medium 28 is more preferably 0.001 mg/ml or higher, even more preferably 0.006 mg/ml or higher, and still more preferably 0.01 mg/ml or higher. Thereby, aggregates 30 can be formed with more numerous kidney cells 24. Furthermore, the concentration of collagen I is more preferably 0.1 mg/ml or less. Thereby, gelation of collagen I can be avoided more reliably. In addition, it is preferable that collagen I to be added to the medium is incorporated at a concentration as low as possible. It is preferable that the concentration of collagen I is adjusted with sterilized water or a medium, which has been adjusted to pH 3.0. It is also preferable that collagen I is added to a medium at a low temperature (for example, room temperature or lower), subsequently the medium is warmed to 37° C., and then the cells are suspended. Thereby, gelation of collagen I can be prevented more reliably.

It is preferable that the culture vessel 26 has been subjected to a non-cell adhesion treatment, or is formed from a non-cell-adhesive material. As a result, aggregates 30 can be formed more reliably. Example of the non-cell adhesion treatment include a non-cell adhesive hydrogel coating treatment, an MPC (2-methacryloyloxyethyl phosphorylcholine) coating treatment, a PROTEOSAVE (registered trademark) SS coating treatment, and a mirror surface polishing treatment on the vessel surface. Examples of the non-cell adhesive material include glass. Furthermore, examples of the non-cell adhesive material include polymer materials such as a low-density polyethylene, a medium-density polyethylene, polyvinyl chloride, a polyethylene-vinyl acetate copolymer, a poly(ethylene-ethyl acrylate) copolymer, a poly(ethylene-methacrylate) copolymer, a poly (ethylene-vinyl acetate) copolymer, and a mixture of two or more kinds of these polymers. For example, a culture bag formed from the polymer material can be used as the culture vessel 26. The cultivation period for kidney cells 24 is preferably 10 days or less (that is, 240 hours or less). As a result, cultivated cells 16 that are in a state in which physiological functions are expressed at a higher level can be obtained. The cultivation conditions are, for example, 37° C. and 5% $CO_2$. It is preferable that during the cultivation period, the medium 28 is exchanged regularly. For example, the medium 28 is exchanged every two days.

Figure 3C:
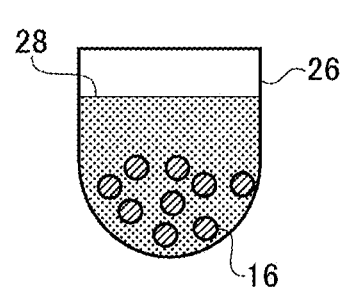

Subsequently, as shown in FIG. 3C, the aggregates 30 formed by the above-mentioned cell cultivation method are separated into individual cultivated cells 16. The separation of the cultivated cells 16 from the aggregates 30 can be carried out by enzymatically treating the aggregates 30 using trypsin/EDTA, Accutase, EDTA, TrypLE Select, or the like. The concentration of the enzyme used for the treatment can be set as appropriate according to the type of the cultivated cells 16. However, in a case in which the enzyme concentration is high, isolation of the cultivated cells 16 is made easy, while there is a high risk that the cell surface proteins of the cultivated cells 16 may be damaged. Accordingly, it is desirable that the enzyme concentration is as low as possible.

Figure 3D:
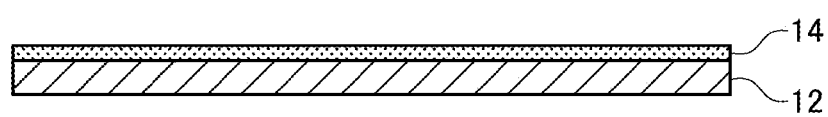

Furthermore, as shown in FIG. 3D, a coating agent containing one or more adhesive molecules selected from the group consisting of laminin molecules, a basement membrane matrix mixture, collagen molecules, and fragments of any of these, is applied on at least a portion of a substrate 12. Thereby, a coating agent layer 14 is formed on the surface of the substrate 12. Meanwhile, the process of isolating the cultivated cells 16 and the process of applying the coating agent can be carried out independently of each other. That is, any one of the two processes may be carried out first, or the two processes may be carried out in parallel.

Figure 3E:
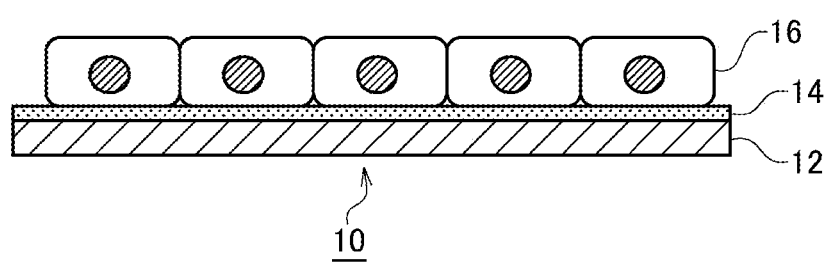

Then, as shown in FIG. 3E, the cultivated cells 16 are seeded on the substrate 12 coated with the coating agent, the cultivated cells 16 are cultivated on the substrate 12, and thereby a single layer structure of the cultivated cells 16 is formed. The cultivated cells 16 are seeded on the substrate 12 such that, for example, a cell density of about $1.0 \times 10^3$ to about $1.0 \times 10^5$ cells/cm$^2$ is obtained. The cultivation period is, for example, from 1 day to 60 days. The cultivated cells 16 are grown to a confluent state on the substrate 12, and then the confluent state is maintained. Furthermore, the cultivated cells 16 are cultivated using, for example, REGM (Lonza, Inc.) as a medium under the conditions of 37° C. and 5% $CO_2$.

Apparatus Using Cell Support Composite

FIG. 4A to FIG. 4F are diagrams schematically illustrating an adoption example of the cell support composite according to an embodiment. In FIG. 4A to FIG. 4F, parts of the structure in which the cell support composite is incorporated are illustrated. The cell support composite 10 according to the present embodiment can be applied to various apparatuses.

Figure 4B:
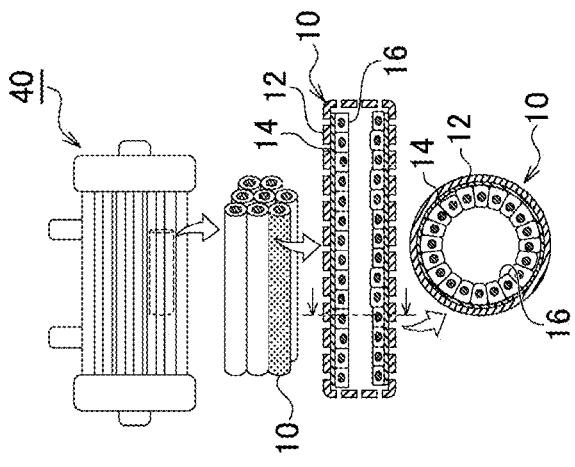
FIG. 4A to FIG. 4F are diagrams schematically illustrating an adoption example of the cell support composite related to an embodiment.
Figure 4A:
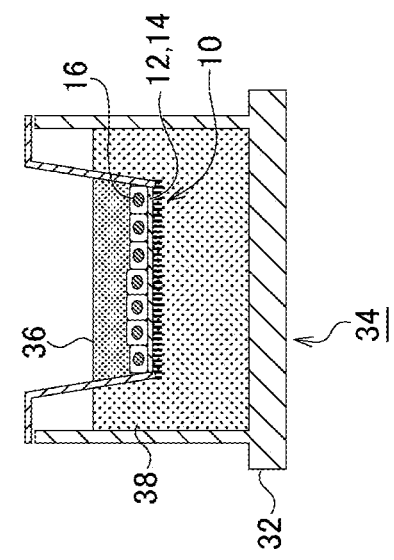

For example, FIG. 4A illustrates a condition in which the cell support composite 10 is incorporated into a first apparatus 34 equipped with a Transwell 32. Since the structure of Transwell 32 is conventionally known, detailed description thereof will not be given here. In the first apparatus 34, a first liquid 36 containing a predetermined substance is supplied to the side where the cultivated cells 16 are disposed. The predetermined substance in the first liquid 36 is taken in by the cultivated cells 16, passes through the cell support composite 10, and migrates to a second liquid 38 located on the opposite side of the first liquid 36 across the cell support composite 10. The first apparatus 34 can be used as, for example, a drug evaluation module for investigating a function of a cell or the uptake and excretion of a drug with a very small amount of liquid.

FIG. 4B illustrates a condition in which a cell support composite 10 that uses a hollow fiber membrane as the substrate 12 has been incorporated into a second apparatus 40. In the second apparatus 40, a coating agent layer 14 and a single layer structure of cultivated cells 16 are formed inside the tubular cavity of a hollow fiber membrane as the substrate 12. In the second apparatus 40, as a liquid is caused to flow into the tubular cavity of the hollow fiber membrane, a predetermined substance present in this liquid can be incorporated into the cultivated cells 16 and caused to migrate out of the tubular cavity of the hollow fiber membrane. The second apparatus 40 can be used as, for example, a bio-artificial kidney module that collects useful substances from blood plasma components filtered through a blood filtering device.

Figures 4D, 4E:
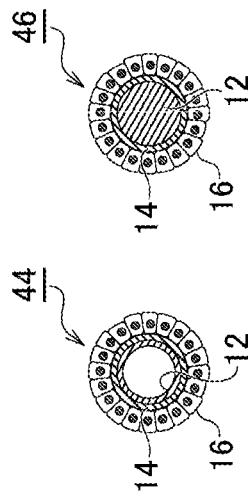
Figure 4F:
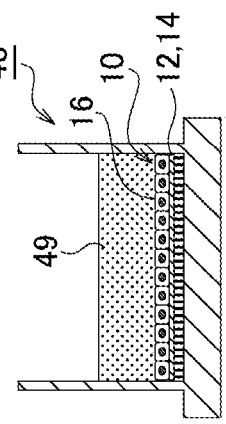
Figure 4C:
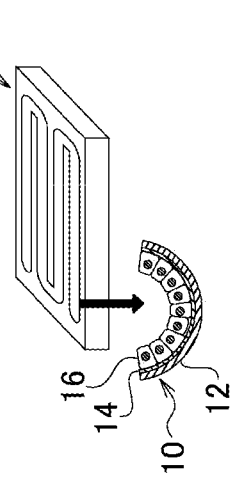

FIG. 4C illustrates a condition in which the cell support composite 10 has been incorporated into a micro flow channel chip 42. In the micro flow channel chip 42, the substrate 12 constitutes a micro flow channel. Furthermore, a coating agent layer 14 and a single layer structure of cultivated cells 16 are formed on the inner wall of the micro flow channel. In the micro flow channel chip 42, a very small amount of liquid flows within the flow channel, that is, on the side where the cultivated cells 16 are disposed. Then, a predetermined substance in the liquid is taken in by the cultivated cells 16. The micro flow channel chip 42 can be used as, for example, a drug evaluation module for investigating a function of a cell or the uptake and excretion of a drug with a very small amount of liquid.

FIG. 4D illustrates a condition in which the cell support composite 10 constitutes a hollow microcarrier 44. Furthermore, FIG. 4E illustrates a condition in which the cell support composite 10 constitutes a solid microcarrier 46. In the hollow microcarrier 44 and the solid microcarrier 46, the substrate 12 constitutes the carrier main body. Then, a coating agent layer 14 and a single layer structure of cultivated cells 16 are formed on the outer surface of the substrate 12. In the hollow microcarrier 44 and the solid microcarrier 46, a very small amount of a liquid flows on the side where the cultivated cells 16 are disposed. Then, a predetermined substance in the liquid is taken in by the cultivated cells 16. The hollow microcarrier 44 and the solid microcarrier 46 can be used as, for example, drug evaluation modules for investigating a function of a cell or the uptake and excretion of a drug with a very small amount of liquid.

FIG. 4F illustrates a condition in which the cell support composite 10 has been incorporated into a well plate 48. On the well plate 48, the cell support composite 10 is disposed at the well bottom. In this state, the cultivated cells 16 face the upper side of the well. In the well plate 48, a very small amount of a liquid 49 is injected into wells. Then, a predetermined substance in the liquid 49 is taken in by the cultivated cells 16. The well plate 48 can be used as, for example, a drug evaluation module for investigating a function of a cell or the uptake and excretion of a drug with a very small amount of liquid. Meanwhile, it is also acceptable that the cell support composite 10 is incorporated into a culture dish (Petri dish or the like), instead of the well plate 48.

The above-mentioned module having the cell support composite 10 incorporated therein is appropriately accommodated into a cartridge as in the case of the second apparatus 40 and used.

As explained above, a method for cultivating cells according to the present embodiment includes cultivating kidney cells 24 in a state of being non-adherent to a culture vessel 26 for a period of 5 days or longer, thereby forming aggregates 30 of kidney cells 24 during the cultivation period, and then cultivating the cells in a state of having formed aggregates 30, for a portion of the period. By cultivating the kidney cells 24 in a suspended state, aggregates 30 can be formed. In other words, the method for cultivating cells according to the present embodiment includes cultivating kidney cells 24 in a state of being non-adherent to a culture vessel 26 and thereby forming aggregates 30 of the kidney cells 24, and the cultivation period is 5 days or longer. By cultivating kidney cells 24 in a state of having formed aggregates 30, the physiological functions of kidney cells 24 that have been deteriorated by cultivation can be restored.

Therefore, according to the cultivation method of the present embodiment, cells that are in a state of exhibiting satisfactory physiological functions compared to conventional cases can be obtained. Furthermore, a high-performance bio-artificial organ or a high-performance in vitro evaluation system can be provided by producing the cell support composite 10 using the highly functional cells thus obtained. Meanwhile, the term "suspended state" means a state in which cells are not adhering to the wall surface of the culture vessel 26. Therefore, the "suspended state" includes a state in which cells are in contact with the wall surface of the culture vessel 26 but can be easily separated apart from the wall surface by a convective flow of the medium 28 or the like.

Furthermore, in the cultivation method of the present embodiment, the aggregates 30 are formed on the first day of cultivation, and the cultivation period of the kidney cells 24 is 10 days or shorter. Accordingly, cultivated cells 16 that are in a state in which their physiological functions are more strongly exhibited can be obtained. Furthermore, generally, when cells continuously maintain an aggregated state for a long period of time, cells remember the state and tend to easily aggregate. In this regard, as the cultivation period is adjusted to be 10 days or shorter, the cultivated cell 16 can be prevented from being not easily isolatable from the aggregates 30, and from becoming easily re-aggregatable after isolation.

In the cultivation method of the present embodiment, the number of kidney cells 24 that constitute the aggregates 30 is from 500 cells/well to 5,000 cells/well. Furthermore, the size of an aggregate 30 is from 100 µm to 350 µm. By adjusting the number of constituent cells to 500 cells/well or more, or adjusting the size to 100 µm or larger, the aggregates 30 being suctioned at the time of medium exchange or the like can be avoided more reliably. Accordingly, the workability of cell cultivation can be enhanced. Furthermore, by adjusting the number of constituent cells to 5,000 cells/well or fewer, or adjusting the size to 350 µm or less, the functions of kidney cells 24 can be restored more reliably. That is, cultivated cells 16 having satisfactory physiological functions can be produced more reliably.

Furthermore, in the cultivation method of the present embodiment, the culture vessel 26 is subjected to a non-cell adhesion treatment, or the culture vessel 26 is formed from a non-cell adhesive material. Accordingly, aggregates 30 of cells can be formed more reliably. Therefore, cultivated cells 16 having physiological functions can be produced more reliably.

The cultivation method of the present embodiment includes addition of collagen I to the medium 28, in other words, addition of a cell suspension containing collagen I to the culture vessel 26. Collagen I acts as an adhesive between kidney cells 24. Therefore, even in a case in which the ability for self-aggregation of the kidney cells 24 is low, aggregates 30 can be formed more reliably. Furthermore, the content of collagen I in the cell suspension is preferably greater than 0.0005 mg/ml and less than 0.15 mg/ml. Accordingly, the effect of promoting the formation of aggregates 30 as provided by collagen I can be exhibited more reliably.

Regarding the technique for forming cell aggregate masses having a low ability for self-aggregation, a method of adding a cell suspension to a high-viscosity medium containing a swellable material, causing the water fraction in the cell suspension to migrate into the high-viscosity medium, and thereby forcibly forming cell aggregate masses may be considered. However, in this method, the operation of forming aggregate masses becomes complicated. Furthermore, separation of the aggregate masses from the high-viscosity medium is difficult, and a cell harvest loss may occur. Furthermore, gel capsules may be formed on the outer surface of the aggregate masses and disturb the supply of oxygen and nutrients to the aggregate masses, particularly the interior of the aggregate masses. In contrast, when collagen I is added to the medium 28 as in the case of the present embodiment, cell aggregate masses having a low ability for self-aggregation can be formed without the occurrence of the above-described problems.

The method for producing a cell support composite 10 according to the present embodiment includes: applying a coating agent containing one or more selected from the group consisting of laminin molecules, a basement membrane matrix mixture, collagen molecules, and fragments of any of these on a substrate 12; separating aggregates 30 of cultivated cells 16 into individual cultivated cells 16; and seeding the cultivated cells 16 onto the substrate 12, cultivating the cultivated cells 16 on the substrate 12, and thereby forming a single layer structure of the cultivated cells 16. As such, when a coating agent containing a predetermined adhesive molecule is applied on a substrate 12 and a coating agent layer 14 is formed, a single layer structure of cultivated cells 16 can be stably formed on the substrate 12. Therefore, a cell support composite 10 in which the stability of the single layer structure of the cultivated cells 16 has been enhanced can be provided. Furthermore, formed on the substrate 12 is a single layer membrane formed from cultivated cells 16 having high physiological functions. Therefore, a highly functional cell support composite 10 can be obtained.

According to the method for producing a cell support composite 10 of the present embodiment, a single layer of cultivated cells 16 is stably obtained. Therefore, it is not necessary to check by a microscopic observation that the cultivated cells 16 have reached confluency on the substrate 12. Furthermore, an artificial membrane can be utilized as the substrate 12. Therefore, a cell support composite 10 having a desired shape can be produced easily. Also, cell support composites 10 having the same structure can be produced in large quantities.

In addition, it may also be considered to use a biological scaffold obtained by decellularizing the small intestine submucosa of human being, sheep, pig, or the like as the substrate. However, since such a biological scaffold is derived from a living body, it is difficult to produce biological scaffolds having the same structure in large quantities. Therefore, the scaffold is not suitable for clinical applications such as an artificial kidney. Furthermore, small intestine submucosa is such that individual tissues have different shapes depending on animal species differences or individual differences. Therefore, the seeding area of cells can also be changed individually. Therefore, it is difficult to control the number of seeded cells. Furthermore, the shape is complicated, and since the submucosa is not a transparent material, observation of cells is difficult. Therefore, the small intestine submucosa is not suitable for the utilization in a drug evaluation system that requires observation of cells.

The present invention is not intended to be limited to the embodiments described above, and it is possible to add various modifications such as design alteration based on the knowledge of a person ordinarily skilled in the art, while embodiments to which such modifications have been added are also included in the scope of the present invention. New embodiments produced by combinations of the above-described embodiments and the following modification examples exhibit the respective effects of the embodiments and modification example to be combined, in combination.

EXAMPLES

Analysis of Gene Expression in Renal Proximal Tubular Epithelial Cells: Test 1

Deterioration of physiological functions in renal proximal tubular epithelial cells was checked by Test 1. First, 100,000 human renal proximal tubular epithelial cells (Lonza, Inc.) were seeded onto a 60-mm Petri dish (Corning Inc.) coated with a gelatin solution (Sigma-Aldrich Corp.). Then, the cells were cultivated using REGM (Lonza, Inc.) as a medium under the conditions of 37° C. and 5% $CO_2$.

mRNAs were extracted from the renal proximal tubular epithelial cells immediately after seeding (that is, zero hours) and day 4 of cultivation (that is, 96 hours) using an RNeasy Mini Kit (QIAGEN NV), and the mRNAs were purified. Subsequently, cDNAs were synthesized from the purified mRNAs using a QuantiTect Reverse Transcription Kit (QIAGEN NV). These cDNAs were used as templates and the amounts of expression of the respective genes of AQP1, CD13, SGLT2, Na/K ATPase, PEPT1, MDR1, OAT1, OCTN2, E-cadherin, and ZO-1 were measured by a real time PCR method using Thermal Cycler Dice Real Time System I (Takara Bio Inc.).

These genes are genes related to the physiological functions of kidney cells. Specifically, AQP1 (aquaporin 1) is a gene encoding a protein that participates in the transportation of water. CD13 (alanyl aminopeptidase) is a gene encoding a protein that participates in the peptidation of proteins. SGLT2 (sodium glucose cotransporter 2) is a gene encoding a protein that participates in the transportation of sodium and glucose. Na/K ATPase is a gene encoding a protein that participates in the transportation of ions. PEPT1 (peptide transporter 1) is a gene encoding a protein that participates in the transportation of peptides. MDR1 (multiple drug resistance 1), OAT1 (organic anion transporter 1), and OCTN2 (organic cation transporter novel 1) are genes encoding proteins that participate in the transportation of drugs. E-cadherin and ZO-1 (zonula occludens-1) are genes encoding proteins that participate in intercellular binding.

For each of the genes, the ratio (day 4/day 0) of the amount of expression on day 4 of cultivation with respect to the amount of expression immediately after seeding was calculated. The results are presented in FIG. 5. FIG. 5 is a diagram showing the changes over time in the amount of gene expression in a case in which cells were adherently cultivated. As shown in FIG. 5, the ratios were less than 1 for all of the genes. That is, the amounts of expression of the various genes on day 4 of cultivation were decreased compared to the amounts immediately after cultivation. From these results, it was found that renal proximal tubular epithelial cells undergo a decrease in the amount of gene expression in two-dimensional cultivation in a Petri dish, that is, undergo dedifferentiation. Furthermore, it is speculated that even immediately after seeding, the physiological functions of the renal proximal tubular epithelial cells are deteriorated to a certain extent.

Non-adherent Cultivation of Renal Proximal Tubular Epithelial Cells: Test 2

The form of cells obtainable at the time of non-adherently cultivating renal proximal tubular epithelial cells was checked by Test 2. First, a plurality of suspensions of human renal proximal tubular epithelial cells that had been dedifferentiated in the same manner as in Test 1, was prepared by varying the cell concentration. The concentration in the respective cell suspensions was set to 5,000, 10,000, 25,000, 50,000, 100,000, or 250,000 cells/ml. 100 µl of each of the cell suspensions was dropped on a 96-well U-bottom plate (Sumitomo Bakelite Co., Ltd.) that had been subjected to a non-cell adhesion treatment, and cells were seeded thereon. Accordingly, the number of cells in the respective plates was adjusted to 500 cells/well, 1,000 cells/well, 2,500 cells/well, 5,000 cells/well, 10,000 cells/well, or 25,000 cells/well. Then, the cells were cultivated using REGM (Lonza, Inc.) as a medium under the conditions of 37° C. and 5% $CO_2$. The medium was exchanged every two days.

Microscopic images of cells on day 3 and day 7 (that is, 72 hours and 168 hours) of cultivation in the respective plates are shown in FIG. 6A. FIG. 6A is a set of optical microscopic images of cells on day 3 and day 7 of non-adherent cultivation. As shown in FIG. 6A, it was verified that renal proximal tubular epithelial cells form aggregates as a result of non-adherent cultivation.

Furthermore, the diameters of aggregates on day 7 after seeding were measured for the respective plates. The diameters of the aggregates were measured using the measurement software of a digital microscope VHX-500 (Keyence Corp.). The diameters, that is, the maximum widths, of ten aggregates in the plates of the respective cell numbers were measured, and the maximum value and the minimum value were determined. The results are presented in FIG. 6B. FIG. 6B is a diagram showing the maximum value and the minimum value of the diameters of aggregates. As shown in FIG. 6B, the approximate diameter of the aggregates was 100 to 180 µm in the case with a number of cells of 500 cells/well (that is, the number of constituent cells of an aggregate was 500). Furthermore, the approximate diameter was 150 to 220 µm in the case with a number of cells of 1,000 cells/well (that is, the number of constituent cells of an aggregate was 1,000). Furthermore, the approximate diameter was 220 to 300 µm in the case with a number of cells of 2,500 cells/well (that is, the number of constituent cells of an aggregate was 2,500). Furthermore, the approximate diameter was 260 to 350 µm in the case with a number of cells of 5,000 cells/well (that is, the number of constituent cells of an aggregate was 5,000). Furthermore, the approximate diameter was 370 to 480 µm in the case with a number of cells of 10,000 cells/well (that is, the number of constituent cells of an aggregate was 10,000). Furthermore, the approximate diameter was 460 to 610 µm in the case with a number of cells of 25,000 cells/well (that is, the number of constituent cells of an aggregate was 25,000).

Furthermore, for the aggregates on day 3, day 7, and day 14 (that is, 72 hours, 168 hours, and 336 hours) of seeding in the respective plates, the number of cells constituting each of aggregates was measured. Specifically, the constituent cells of the aggregates were unified with a 0.1% trypsin solution, and then the number of cells was measured for twenty aggregates using a TC20 fully automated cell counter (Bio-Rad Laboratories, Inc.). The average value thereof was designated as the number of constituent cells of the aggregates. The results are presented in FIG. 6C. FIG. 6C is a diagram showing the changes over time in the number of constituent cells of the aggregates. As shown in FIG. 6C, it was verified that the number of constituent cells of the aggregates almost did not have any change over 14 days. Meanwhile, it was also verified that the diameter of the aggregates almost did not have any change over 14 days.

Measurement of Amount of Gene Expression in Renal Proximal Tubular Epithelial Cells Constituting Aggregates: Test 3

Restoration of physiological functions by non-adherent cultivation of renal proximal tubular epithelial cells was checked by Test 3. First, a suspension of dedifferentiated human renal proximal tubular epithelial cells was prepared and cultivated in the same manner as in Test 2. Furthermore, 100 µl of the cell suspension having its cell density adjusted to 10,000 cells/ml was dropped on a 96-well flat-bottom plate (Corning Inc.) coated with a gelatin solution (Sigma-Aldrich Corp.), and thereby the cells were seeded. Therefore, the number of cells was 1,000 cells/well. Then, the cells were cultivated using REGM (Lonza, Inc.) as a medium under the conditions of 37° C. and 5% $CO_2$. The medium was exchanged every two days. This was designated as Comparative Example. In Comparative Example, the plate was subjected to gelatin coating, that is, an adhesion treatment. Furthermore, since the well bottom face was flat bottom, cells were seeded at an almost equal interval, and thereby the formation of aggregates was inhibited. Therefore, the cells were cultivated in a state in which the cells were adherent to the plate, and aggregates were not formed.

mRNAs were extracted, using an RNeasy Mini Kit (QIAGEN NV), from the renal proximal tubular epithelial cells immediately after seeding (that is, zero hours) and the renal proximal tubular epithelial cells constituting aggregates on day 3 and day 7 (that is, 72 hours and 168 hours) of cultivation, and the mRNAs were purified. Subsequently, cDNAs were synthesized from the purified mRNAs using a QuantiTect Reverse Transcription Kit (QIAGEN NV). These cDNAs were used as templates, and the amounts of expression of the respective genes of AQP1, SGLT2, and OAT1 were measured by a real time PCR method using a Thermal Cycler Dice Real Time System I (Takara Bio Inc.).

For each of the genes, the ratio (day 3/day 0) of the amount of expression on day 3 of cultivation with respect to the amount of expression immediately after seeding, and the ratio (day 7/day 0) of the amount of expression on day 7 of cultivation with respect to the amount of expression immediately after seeding were calculated. The results are presented in FIG. 7. FIG. 7 is a diagram showing the changes over time in the amount of gene expression in the cells constituting aggregates.

As shown in FIG. 7, with regard to AQP1 gene and SGLT2 gene, it was verified that with any number of cells at any day of cultivation, the amount of expression was larger in a case in which cells were non-adherently cultivated, compared to Comparative Example in which cells were adherently cultivated. Particularly, on day 7 of cultivation, the tendency was conspicuous. With regard to OAT1 gene, the amount of expression was larger in Comparative Example on day 3 of cultivation; however, on day 7 of cultivation, the amount of expression was larger when cells were non-adherently cultivated, except for the case with a number of cells of 25,000 cells/well. Therefore, it was verified that the physiological functions of cells tend to be restored in a case in which the cells are non-adherently cultivated, compared to the case in which the cells are adherently cultivated.

Furthermore, from the results of day 7 of cultivation of the various genes, it was verified that in a case in which the number of cells was from 500 cells/well to 5,000 cells/well, the amounts of expression of AQP1 gene and OAT1 gene were noticeably increased. From this, it was verified that physiological functions become more satisfactory by adjusting the number of cells to the above-described range.

Analysis of Changes Over Time in Amount of Gene Expression in Renal Proximal Tubular Epithelial Cells Constituting Aggregates: Test 4

Restoration of physiological functions by non-adherent cultivation of renal proximal tubular epithelial cells was checked by Test 4. First, a suspension of dedifferentiated human renal proximal tubular epithelial cells was prepared in the same manner as in Test 2, and the cells were cultivated. Meanwhile, only a cell suspension having its cell concentration adjusted to 10,000 cells/ml was used (therefore, the number of cells was 1,000 cells/well).

mRNAs were extracted from renal proximal tubular epithelial cells immediately after seeding (that is, zero hours) and renal proximal tubular epithelial cells constituting aggregates on days 3, 4, 5, 6, 7, 8, 10, 12, and 14 (that is, 72, 96, 120, 144, 168, 192, 240, 288, and 336 hours) of cultivation using an RNeasy Mini Kit (QIAGEN NV), and the mRNAs were purified. Subsequently, cDNAs were synthesized from the purified mRNAs using a QuantiTect Reverse Transcription Kit (QIAGEN NV). These cDNAs were used as templates, and the amounts of expression of the respective genes of AQP1, SGLT2, and OAT1 were measured by a real time PCR method using a Thermal Cycler Dice Real Time System I (Takara Bio Inc.)

For each of the genes, the ratios (day M/day 0) of the amount of expression of day M (M=3, 4, 5, 6, 7, 8, 10, 12, and 14) of cultivation with respect to the amount of expression immediately after seeding were calculated. The results are presented in FIG. 8. FIG. 8 is a diagram showing the changes over time in the amount of gene expression in the cells constituting aggregates.

As shown in FIG. 8, with regard to AQP1 gene and OAT1 gene, it was confirmed that the amounts of expression rapidly increased on day 5 of cultivation. Also with regard to SGLT2 gene, a high amount of expression was obtained on day 5 of cultivation. From this, it was verified that cells having improved physiological functions were obtained by adjusting the cultivation period of renal proximal tubular epithelial cells to 5 days or longer. Furthermore, with regard to AQP1 gene and OAT1 gene, it was verified that after 10 days of cultivation, the amounts of expression changed to a declining tendency. From this, it was verified that the cultivation period for the renal proximal tubular epithelial cells is more preferably 10 days or less. Meanwhile, the amounts of expression of AQP1 gene and OAT1 gene had higher values even on day 12 and day 14 of cultivation, compared to the value obtained immediately after cultivation. Isolation of Cells from Aggregates and Recultivation: Test 5

3 ml of a suspension of human renal proximal tubular epithelial cells that had been dedifferentiated in the same manner as in Test 1, was dropped on a 60-mm Petri dish (Sumitomo Bakelite Co., Ltd.; cultivation area 21 cm$^2$) that had been subjected to a non-adhesion treatment, and the cells were seeded. The cell concentration in the cell suspension was set to 100,000 cells/ml. Therefore, the cells density was about 14,300 cells/cm$^2$. Then, the cells were cultivated using REGM (Lonza, Inc.) as a medium under the conditions of 37° C. and 5% $CO_2$. The medium was exchanged every two days. The aggregates on day 7 (that is, 168 hours) of cultivation were collected in a 50-ml tube and were washed with PBS. Subsequently, a portion of the aggregates was treated with 0.1% trypsin/EDTA (Thermo Fisher Scientific Inc.). The other portion of the aggregates was treated with Accutase (Innovative Cell Technologies, Inc.). The treatment conditions were set to 37° C. and 10 minutes. Subsequently, cells constituting aggregates were separated by a pipetting treatment.

Unified cells were re-seeded on a 100-mm Petri dish (Corning Inc.) coated with a gelatin solution (Sigma-Aldrich Corp.). The seeding density of the cells was set to 14,300 cells/cm$^2$. Then, the cells were cultivated using REGM (Lonza, Inc.) as a medium under the conditions of 37° C. and 5% $CO_2$. The medium was exchanged every two days.

Figure 9:
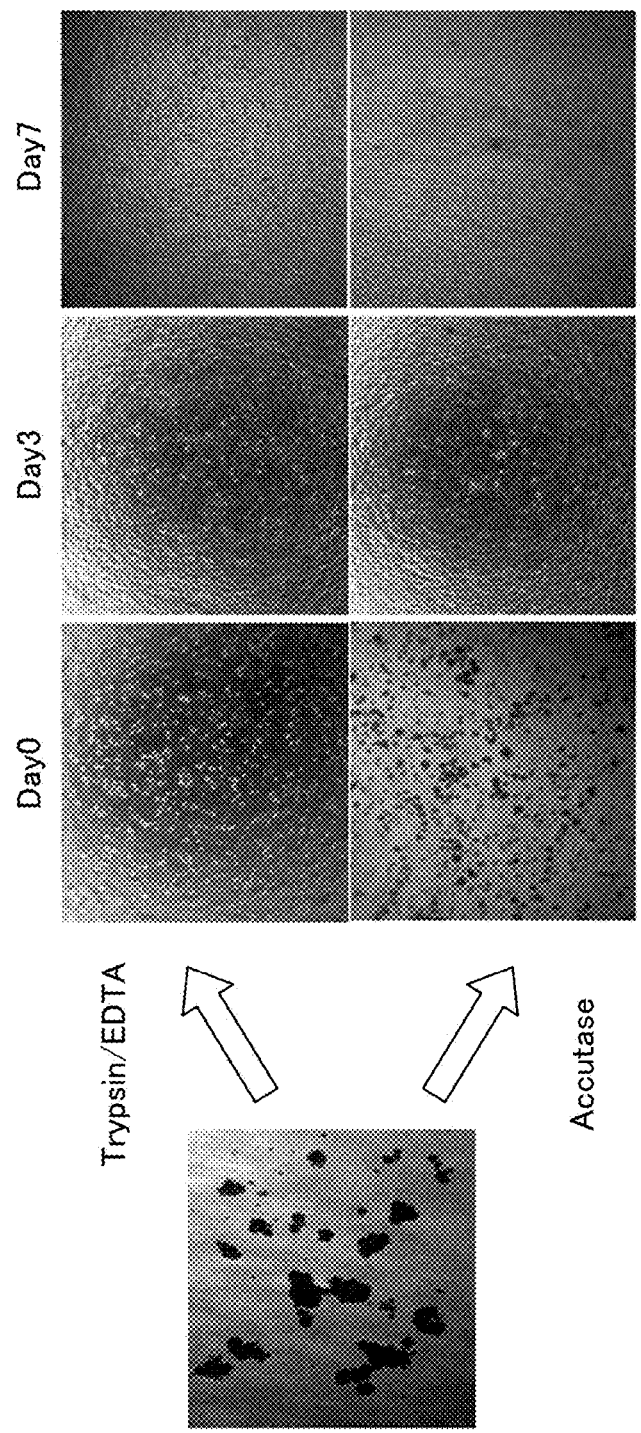
FIG. 9 is a set of optical microscopic images obtained on days 0, 3, and 7 of re-seeding of the cells separated from aggregates.

Microscopic images of the cells on day 0, day 3, and day 7 (that is, 0 hours, 72 hours, and 168 hours) of re-seeding are shown in FIG. 9. FIG. 9 is a set of optical microscopic images on day 0, day 3, and day 7 of re-seeding of cells separated from aggregates. As shown in FIG. 9, it was verified that cells when aggregates of renal proximal tubular epithelial cells are subjected to an enzyme treatment with trypsin, Accutase, or the like, the cells can be unified. It was also verified that when unified cells are re-seeded and cultivated, the cells proliferate to a confluent state. Thereby, it was verified that a cell support composite can be produced using cells having their physiological functions restored by non-adherent cultivation.

Meanwhile, the present inventors have confirmed that when dedifferentiated renal proximal tubular epithelial cells are seeded on a 60-mm Petri dish (Sumitomo Bakelite Co., Ltd.) that has been subjected to a non-adhesion treatment and are cultivated for 3 days, the cells form aggregates on day 1 of cultivation even on a Petri dish. The cell density in this case was set to 1,500 cells/cm$^2$ and 15,000 cells/cm$^2$. Analysis of Relationship between Cell Lot with the Number of Subcultures and the Aggregate Formation: Test 6

It was checked by Test 6 that renal proximal tubular epithelial cells may not form aggregates depending on the cell lot or the number of subcultures. First, lots A to E of human renal proximal tubular epithelial cells (Lonza, Inc.) were prepared. Furthermore, for each of the lots, a lot in which the number of subcultures was two times, and a lot in which the number of subcultures was three times were prepared. For each of the lots thus prepared, 100 μl of a cell suspension having the cell concentration adjusted to 20,000 cells/ml was seeded on a 96-well non-adhesive V-bottom plate (Sumitomo Bakelite Co., Ltd.). Then, the cells were cultivated in a suspended state using REGM (Lonza, Inc.) as a medium under the conditions of 37° C. and 5% $CO_2$. Thereby, regarding the number of subcultures for each lot, the number of subcultures for a lot of two times became three times, and the number of subcultures for a lot of three times became four times.

Figure 10:
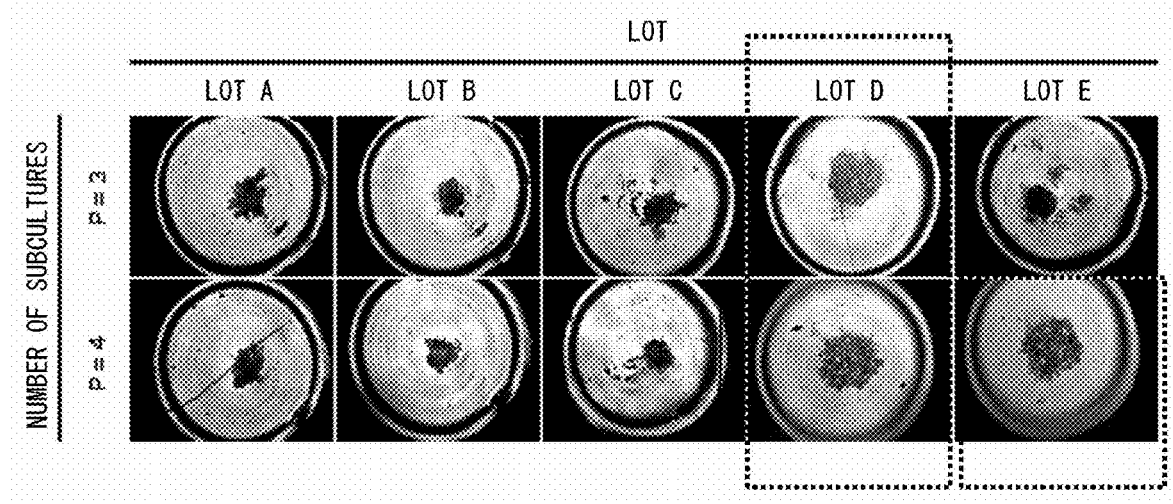
FIG. 10 is a set of optical microscopic images obtained after 24 hours from the seeding of cells of different lots and different numbers of subcultures.

Microscopic images of the cells after a lapse of 24 hours from seeding for the respective lots are shown in FIG. 10. FIG. 10 is a set of optical microscopic images after 24 hours from the seeding of cells of different lots and different numbers of subcultures. As shown in FIG. 10, it was verified that the ability for self-aggregation of renal proximal tubular epithelial cells varies, or is changed, depending on the lot or the number of subcultures. More specifically, in lot D, precipitation and accumulation of cells were observed in both the case of three times of subculture (P=3) and the case of four times of subculture (P=4); however, the cells did not form aggregates. In lot E, despite that the cells formed aggregates in the case of three times of subculture, the cells did not form aggregates in the case of four times of subculture.
Measurement of Amount of Gene Expression in Renal Proximal Tubular Epithelial Cells with Different Aggregation States: Test 7

Restoration of physiological functions by the aggregate formation of renal proximal tubular epithelial cells was checked by Test 7. First, lots A to E with two times of subculture and three times of subculture were prepared in the same manner as in Test 6. For each lot, 100 μl of a cell suspension having a cell concentration of 20,000 cells/ml was seeded onto a 96-well non-adhesive V-bottom plate (Sumitomo Bakelite Co., Ltd.). Then, the cells were cultivated under the same conditions as those of Test 6. As the result, similarly to Test 6, aggregates were formed in lots A to C with three times and four times of subculture and lot E with three times of subculture. On the other hand, aggregates were not formed in lot D with three times and four times of subculture and lot E with four times of subculture.

mRNAs were extracted from the renal proximal tubular epithelial cells after 8 days of cultivation using an RNeasy Mini Kit (QIAGEN NV), and the cells were purified. Subsequently, cDNAs were synthesized from the purified mRNAs using a QuantiTect Reverse Transcription Kit t (QIAGEN NV). These cDNAs were used as templates, and the amounts of expression of OAT1 gene were measured by a real time PCR method using a Thermal Cycler Dice Real Time System I (Takara Bio Inc.).

Figure 11:
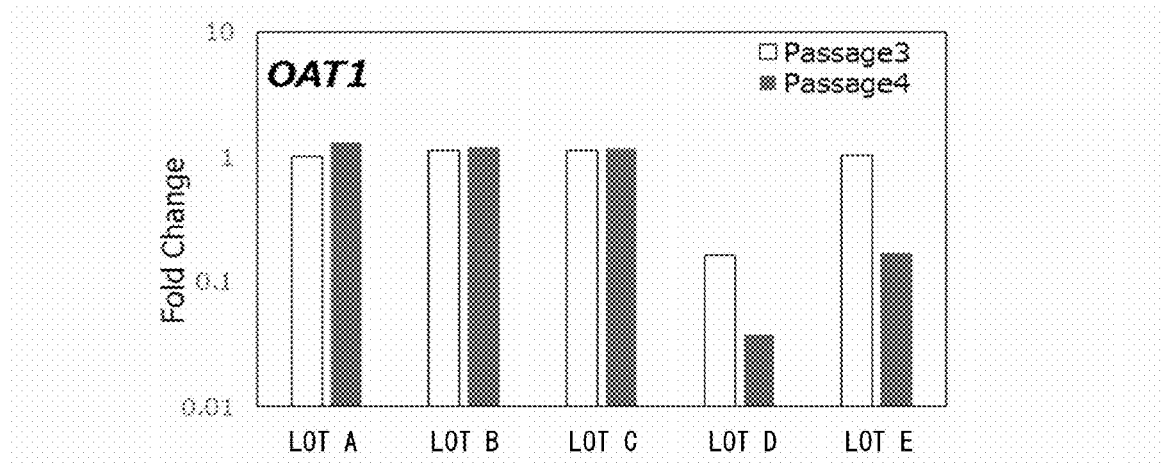
FIG. 11 is a diagram showing the amount of expression of OAT1 gene in cells in different states of aggregation.

The ratio (Fold Change) of the amount of expression of OAT1 gene in each lot with each number of subcultures with respect to the amount of expression of OAT1 gene in lot A with three times of subculture was calculated. The results are presented in FIG. 11. FIG. 11 is a diagram showing the amount of expression of OAT1 gene in cells of different aggregation states. As shown in FIG. 11, in lots A to C with three times and four times of subculture and in lot E with three times of subculture, where aggregates had been formed, there was no large difference in the amounts of expression of OAT1 gene in the renal proximal tubular epithelial cells. On the other hand, in lot D with three times and four times of subculture and lot E with four times of subculture, where aggregates were not formed, it was verified that the amount of expression of OAT1 gene was low compared to the case in which aggregates were formed.

Selection of Substance Capable of Promoting Aggregate Formation: Test 8

Substances capable of promoting self-aggregation of renal proximal tubular epithelial cells were selected by Test 8. Specifically, a cell suspension having a cell concentration of 20,000 cells/ml was prepared using the human renal proximal tubular epithelial cells (Lonza, Inc.) of lot D (number of subcultures: three times), for which it was confirmed by Tests 6 and 7 that self-aggregation did not occur. 100 µl of this cell suspension was seeded onto a 96-well non-adhesive V-bottom plate (Sumitomo Bakelite Co., Ltd.). Furthermore, collagen I, gelatin, MATRIGEL®, laminin 511-E8, collagen IV, laminin 521, and fibronectin, which are representative cell adhesion factors, were added to various wells. With regard to the concentration of each cell adhesion factor, the concentrations of collagen I and collagen IV were adjusted to 0.01 mg/ml and 0.3 mg/ml. The concentration of gelatin was adjusted to 0.01 mg/ml and 0.5 mg/ml. The concentrations of MATRIGEL®, laminin 511-E8, and fibronectin were adjusted to 0.01 mg/ml and 0.1 mg/ml. The concentration of laminin 521 was adjusted to 0.01 mg/ml and 0.05 mg/ml. Furthermore, as a control experiment zone (control), wells where cell adhesion factors were not added were prepared. Then, the cells were cultivated in a suspended state using REGM (Lonza, Inc.) as a medium under the conditions of 37° C. and 5% $CO_2$.

Figure 12:
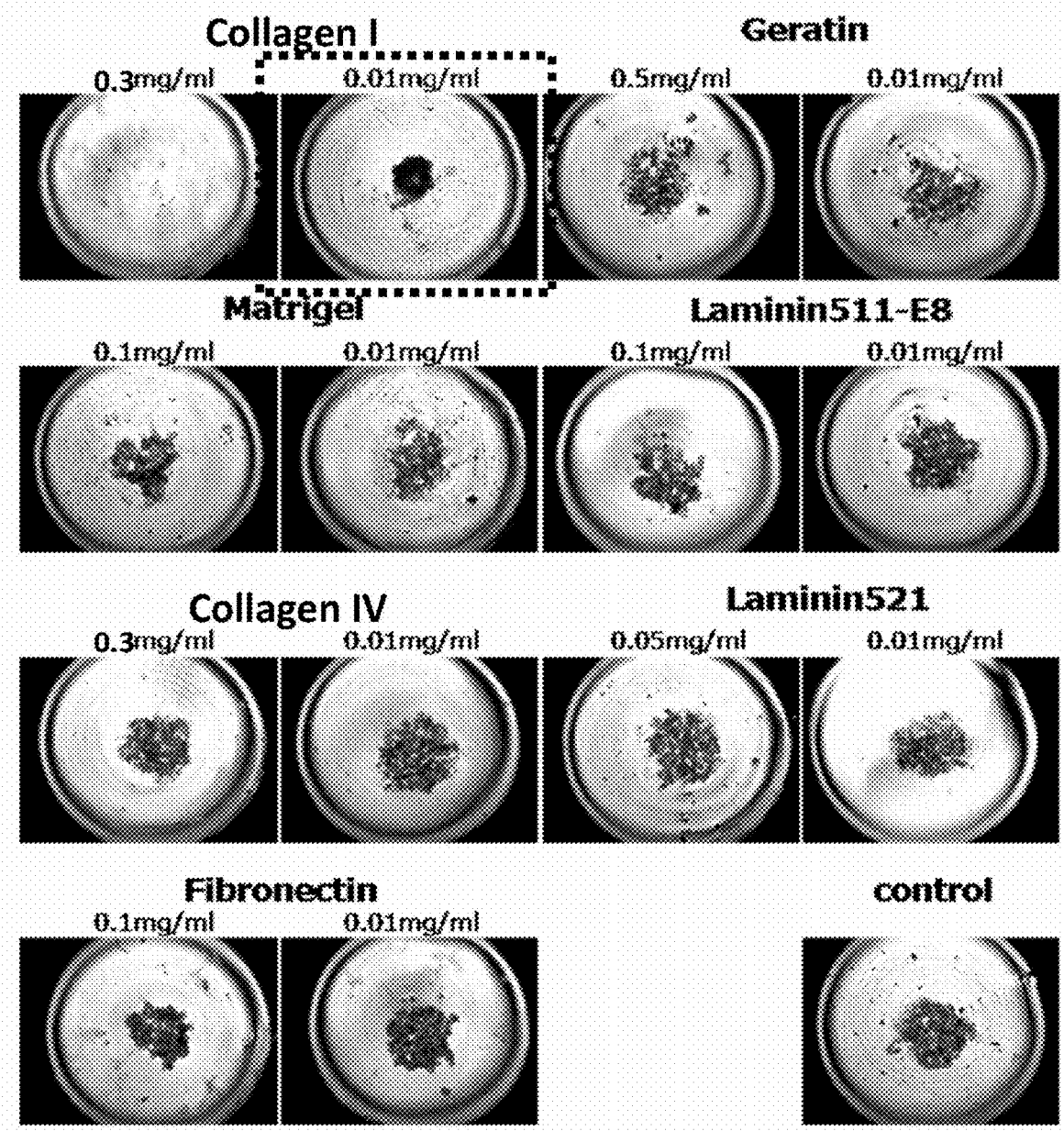
FIG. 12 is a set of optical microscopic images obtained after 24 hours from seeding of cell suspensions having different cell adhesion factors added thereto.

Microscopic images of cells after a lapse of 24 hours from seeding in the respective wells are shown in FIG. 12. FIG. 12 is a set of optical microscopic images after 24 hours from the seeding of cell suspensions to which various cell adhesion factors were added. As shown in FIG. 12, it was verified that when cells were cultivated by adding collagen I to a concentration of 0.01 mg/ml to a suspension of renal proximal tubular epithelial cells that did not undergo self-aggregation, self-aggregation of the cells was promoted, and aggregates were formed. In a case in which a cell adhesion factor other than collagen I was added, cell aggregates were not formed, similarly to the control experiment zone where no cell adhesion factor was added.

Analysis of Concentration of Collagen I: Test 9

The correlation between the concentration of collagen I and the cell state was checked by Test 9. A plurality of cell suspensions having different cell concentrations was prepared using the human renal proximal tubular epithelial cells (Lonza, Inc.) of lot D (number of subcultures: three times), for which it was confirmed by Tests 6 and 7 that self-aggregation did not occur. The cell concentration in the respective cell suspensions was adjusted to 5,000, 10,000, 25,000, and 100,000 cells/ml. 100 µl of each cell suspension was seeded onto a 96-well non-adhesive V-bottom plate (Sumitomo Bakelite Co., Ltd.). Accordingly, the number of cells in each of the plates was 500 cells/well, 1,000 cells/well, 2,500 cells/well, or 10,000 cells/well.

Furthermore, collagen I was added to the wells of various cell suspensions. Collagen I was added such that the concentration would be 0.3, 0.15, 0.1, 0.06, 0.03, 0.01, 0.006, 0.003, 0.001, or 0.0005 mg/ml. Furthermore, as a control experiment zone (control), wells where collagen I was not added (0 mg/ml) were prepared. Then, the cells were cultivated in a suspended state using REGM (Lonza, Inc.) as a medium under the conditions of 37° C. and 5% $CO_2$.

Figures 13A, 13B:
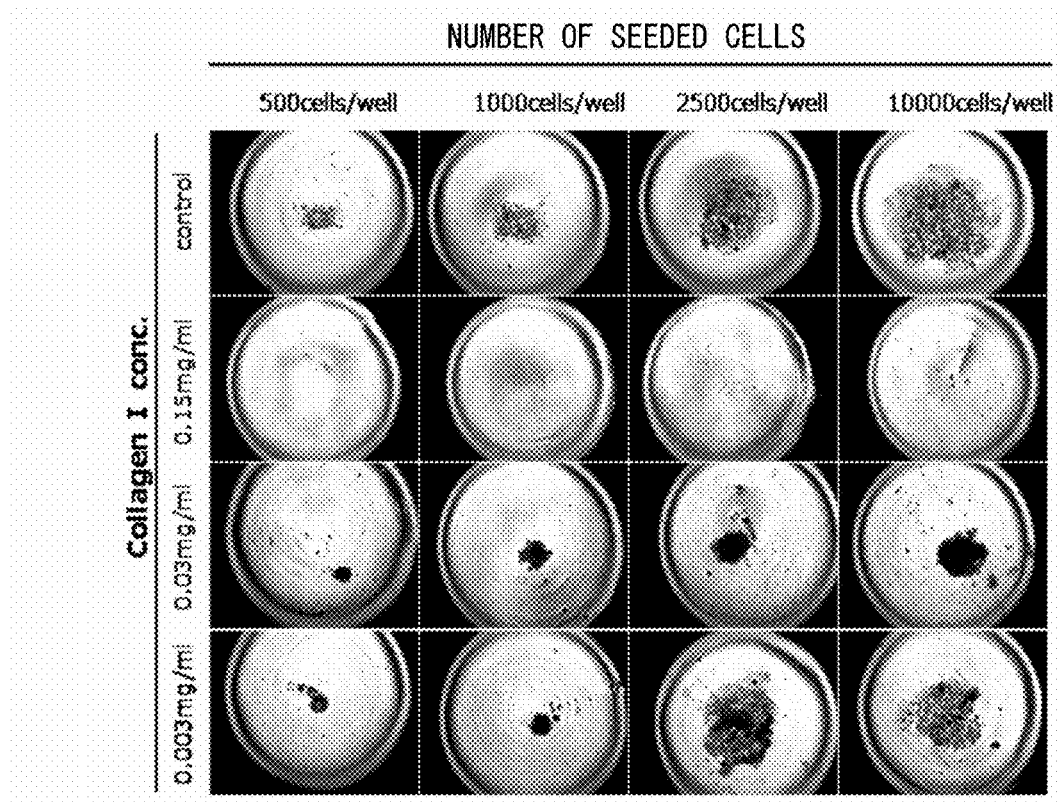
FIG. 13A is a set of optical microscopic images obtained 24 hours after seeding of cell suspensions having collagen I at various concentrations added thereto.
FIG. 13B is a diagram showing the relationship between the concentration of collagen I and the presence or absence of aggregate formation.

Microscopic images of renal proximal tubular epithelial cells cultivated for 24 hours in a medium having a collagen I concentration of 0, 0.15, 0.03, or 0.003 mg/ml are presented in FIG. 13A. FIG. 13A is a set of optical microscopic images obtained 24 hours after seeding of cell suspensions to which collagen I had been added at various concentrations. Furthermore, whether cell aggregates had been formed after being cultivated for 24 hours at various collagen I concentrations was checked from microscopic images. The results are presented in FIG. 13B. FIG. 13B is a diagram showing the relationship between the concentration of collagen I and the presence or absence of aggregate formation. In FIG. 13B, the symbol "O" represents that aggregates were formed, and the symbol "X" represents that aggregates were not formed.

As shown in FIG. 13A and FIG. 13B, it was verified that promotion of self-aggregation of renal proximal tubular epithelial cells by collagen I tends to be affected by the concentration of collagen I and the number of cells. A tendency that when the number of cells constituting aggregates increased, the amount of collagen I needed for promoting aggregation increased, was observed.

More specifically, in the plates with a number of cells of 500 cells/well and 1,000 cells/well, aggregates were not formed at a collagen I concentration of 0.0005 mg/ml, and aggregates were formed at a collagen I concentration of 0.001 mg/ml. From this, it was verified that the formation of aggregates is promoted more reliably when the collagen I concentration is higher than 0.0005 mg/ml, or 0.001 mg/ml or higher. Furthermore, in a case in which the collagen I concentration was 0.0005 mg/ml or lower, it was verified that additional conditions such as adjustment of the number of cells are required in order to form aggregates.

Furthermore, in the plate with a number of cells of 2,500 cells/well, aggregates were not formed at a collagen I concentration of 0.003 mg/ml, and aggregates were formed at a collagen I concentration of 0.006 mg/ml. From this, it was verified that when the collagen I concentration is higher than 0.003 mg/ml or 0.006 mg/ml or higher, aggregates of a wider range of the number of cells are formed. Furthermore, in the plate with a number of cells of 10,000 cells/well, aggregates were not formed at a collagen I concentration of 0.006 mg/ml, and aggregates were formed at a collagen I concentration of 0.01 mg/ml. From this, it was verified that when the collagen I concentration is higher than 0.006 mg/ml or 0.01 mg/ml or higher, aggregates of a wider range of the number of cells are formed.

Furthermore, in all of the plates with any number of cells, aggregates were not formed at a collagen I concentration of 0.15 mg/ml, and aggregates were formed at a collagen I concentration of 0.1 mg/ml. At a collagen I concentration of 0.15 mg/ml, collagen I gelated in the medium and was not dispersed therein. From this, it was verified that when the collagen I concentration is lower than 0.15 mg/ml or 0.1 mg/ml or lower, the formation of aggregates is promoted more reliably. Furthermore, in a case in which the collagen I concentration is 0.15 mg/ml or higher, it was verified that additional conditions are needed in order to avoid gelation of collagen I.

Verification of Aggregation Promoting Effect of Collagen I: Test 10

The effect of promoting the formation of cell aggregates by addition of collagen I was checked by Test 10. Specifically, lots A to E with two times of subculture and three times of subculture were prepared in the same manner as in Tests 6 and 7. For each lot, 100 µl of a cell suspension having a cell concentration of 20,000 cells/ml was seeded onto a 96-well non-adhesive V-bottom plate (Sumitomo Bakelite Co., Ltd.). For the preparation of the cell suspension, medium REGM (Lonza, Inc.) having collagen I added thereto was used. Collagen I was added so as to obtain a concentration of 0.005 mg/ml. Then, the cells were cultivated in a suspended state under the conditions of 37° C. and 5% $CO_2$.

Figure 14:
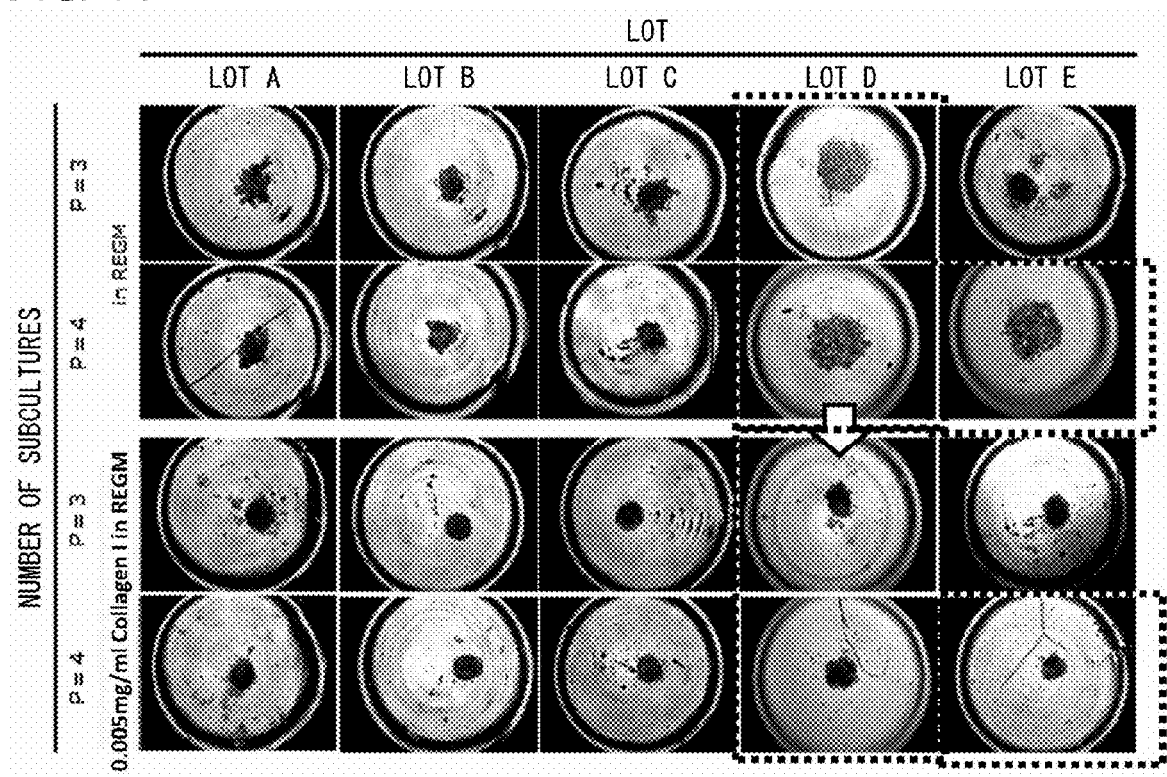
FIG. 14 is a set of optical microscopic images obtained after 24 hours from the seeding of cell suspensions having collagen I added thereto and cell suspensions without addition of collagen I.

Microscopic images of cells after a lapse of 24 hours from seeding in the respective plates are shown in FIG. 14. FIG. 14 is a set of optical microscopic images after 24 hours from seeding of a cell suspension to which collagen I was added and a cell suspension to which collagen I was not added. In FIG. 14, the results under "in REGM" in the upper row are the results of Test 6, and these are the same as those in FIG. 10. The results under "0.005 mg/ml Collagen I in REGM" in the lower row are results of Test 10. As shown in FIG. 14, in lot D with three times of subculture and four times of subculture and lot E with four times of subculture, it was verified that aggregates were not formed in the case where collagen I was not added; however, aggregates were formed when collagen I was added. Furthermore, it was verified that in other lots where aggregates were formed even in the case where collagen I was not added, the aggregated state of the cells was improved by the addition of collagen I, and the aggregates acquired a more regular spherical shape.

Furthermore, mRNAs were extracted from renal proximal tubular epithelial cells after 8 days of cultivation using an RNeasy Mini Kit (QIAGEN NV), and the mRNAs were purified. Subsequently, cDNAs were synthesized from the purified mRNAs using a QuantiTect Reverse Transcription Kit t (QIAGEN NV). These cDNAs were used as templates, and the amount of expression of OAT1 gene was measured by a real time PCR method using a Thermal Cycler Dice Real Time System I (Takara Bio Inc.).

Figure 15A:
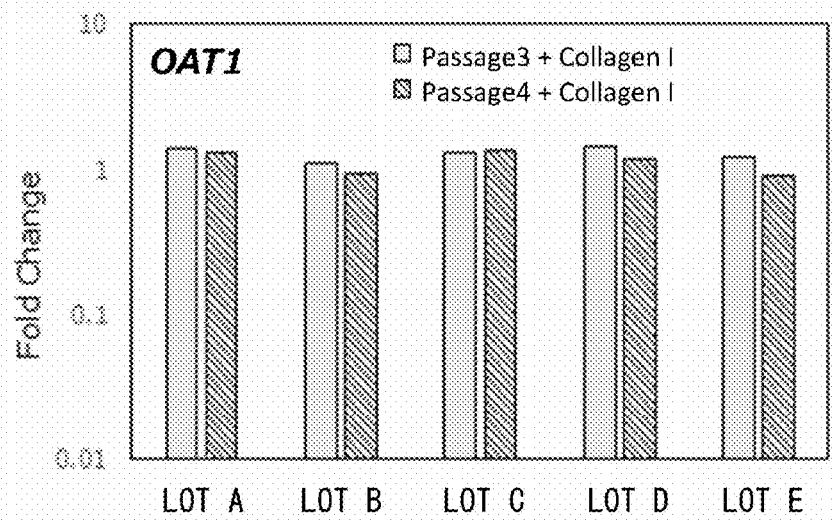
FIG. 15A is a diagram showing the amount of expression of OAT1 gene in cells cultivated with collagen I added thereto.
Figure 15B:
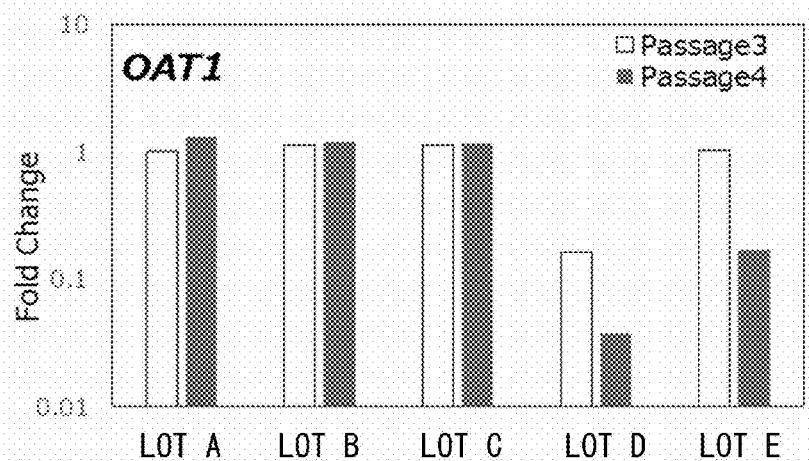
FIG. 15B is a diagram showing the amount of expression of OAT1 gene in cells cultivated without addition of collagen I.

The ratio (Fold Change) of the amount of expression of OAT1 gene in each lot with each number of subcultures with respect to the amount of expression of OAT1 gene in lot A with three times of subculture under non-addition of collagen I was calculated. The results are presented in FIG. 15A. FIG. 15A is a diagram showing the amount of expression of OAT1 gene in cells that were cultivated with added collagen I. Furthermore, the results of Test 7 are presented in FIG. 15B for a comparison. FIG. 15B is a diagram showing the amount of expression of OAT1 gene in cells that were cultivated without adding collagen I. FIG. 15B is the same as FIG. 11.

As shown in FIG. 15B, in lot D with three times of subculture and four times of subculture and lot E with four times of subculture, where aggregates were not formed, the amount of expression of OAT1 gene was low compared to the lots where aggregates were formed. In contrast, aggregates were formed even in these lots under addition of collagen I. Therefore, as shown in FIG. 15A, it was verified that also in lot D with three times of subculture and four times of subculture and lot E with four times of subculture, OAT1 gene was expressed to the same extent as that of other lots where aggregates were formed.

That is, it was verified that under addition of collagen I, self-aggregation of kidney cells was promoted, irrespective of the lot of cells or the number of subcultures, and aggregates were formed. Furthermore, as a result, it was verified that the physiological functions of kidney cells were enhanced.

What is claimed is:

1. A cell cultivation method, comprising:
   cultivating primary cultured kidney cells which are dedifferentiated in a state of being non-adherent to a culture vessel for a period of 5 days or longer,
   forming aggregates of the kidney cells during the cultivation period, then cultivating the kidney cells in a state of having formed aggregates during a portion of the period, and thereby restoring physiological functions of the kidney cells,
   wherein the primary cultured kidney cells are primary cultured renal proximal tubular epithelial cells, wherein a percentage of the primary cultured renal proximal tubular epithelial cells in the primary cultured kidney cells is 83% or more.

2. The cell cultivation method according to claim 1, wherein the aggregates are formed on the first day of cultivation, and the cultivation period for the kidney cells is 14 days or shorter.

3. The cell cultivation method according to claim 1, wherein a number of the kidney cells constituting the aggregates is from 500 to 5,000.

4. The cell cultivation method according to claim 1, wherein the aggregates have a size of from 150 µm to 350 µm.

5. The cell cultivation method according to claim 1, wherein the culture vessel has been subjected to a non-cell adhesion treatment or is formed from a non-cell adhesive material.

6. The cell cultivation method according to claim 1, wherein the kidney cells are cultivated in a medium containing collagen I.

7. The cell cultivation method according to claim 6, wherein a concentration of collagen I in the medium is higher than 0.0005 mg/ml and lower than 0.15 mg/ml.

8. The cell cultivation method according to claim 6, wherein the concentration of the collagen I in the medium is from 0.006 mg/ml to 0.1 mg/ml.

9. The cell cultivation method according to claim 1, wherein the restoring the physiological functions of the kidney cells includes increasing an amount of expression of OAT1 gene.

10. The cell cultivation method according to claim 1, wherein the primary cultured kidney cells are primary cultured human renal proximal tubular cells.

11. A cell cultivation method, comprising:
    cultivating primary cultured kidney cells which are dedifferentiated in a state of being non-adherent to a culture vessel; and
    forming aggregates of the kidney cells during the cultivation period, then cultivating the kidney cells in a state of having formed aggregates during a portion of the period, and thereby restoring the physiological functions of the kidney cells,
    wherein the primary cultured kidney cells are primary cultured renal proximal tubular epithelial cells, wherein a percentage of the primary cultured renal proximal tubular epithelial cells in the primary cultured kidney cells is 83% or more.

12. The cell cultivation method according to claim 11, wherein the primary cultured kidney cells are primary cultured human renal proximal tubular cells.

* * * * *